United States Patent [19]
Hori et al.

[11] Patent Number: 5,597,820
[45] Date of Patent: Jan. 28, 1997

[54] 1,4-BENZOXAZINE DERIVATIVE AND PHARMACEUTICAL COMPOSITIONS CONTAINING THE SAME

[75] Inventors: Manabu Hori; Ikuo Watanabe; Hiroshi Ohtaka; Kengo Harada, all of Osaka-fu; Joji Maruo; Tominori Morita, both of Nara-ken; Takeshi Yamamoto; Hisayoshi Tsutsui, both of Osaka-fu, all of Japan

[73] Assignee: Kanebo, Ltd., Toyko-to, Japan

[21] Appl. No.: 577,348

[22] Filed: Dec. 22, 1995

[30] Foreign Application Priority Data

Dec. 27, 1994 [JP] Japan .................... 6-340044
Jul. 7, 1995 [JP] Japan .................... 7-195939

[51] Int. Cl.$^6$ .................... A61K 31/535; C07D 265/36
[52] U.S. Cl. .................... 514/230.5; 544/105
[58] Field of Search .................... 544/105; 514/230.5

[56] References Cited

U.S. PATENT DOCUMENTS 3,313,813  4/1967  Cragoe, Jr. .................... 260/250

FOREIGN PATENT DOCUMENTS

| | | |
|---|---|---|
| 0073505 | 8/1982 | European Pat. Off. . |
| 0416499 | 9/1990 | European Pat. Off. . |
| 0556672A1 | 8/1993 | European Pat. Off. . |
| 0577024A1 | 1/1994 | European Pat. Off. . |
| 0589336A1 | 7/1994 | European Pat. Off. . |
| 0604852A1 | 7/1994 | European Pat. Off. . |

OTHER PUBLICATIONS

"Na$^+$/H$^+$ exchange and growth factor-induced cytosolic pH changes. Role in cellular proliferation", *Biochimica et Biophysica Acta*, 988 (1989) pp. 73–97, Grinstein et al.

"Effects of New Na$^+$/h$^+$ Antiportner Inhibitor on Postischemic Reperfusion in Pig Heart", *Journal of Cardiovascular Pharmacology*, 23 (1994), pp. 72–78, Sack et al.

"Salt–Sensitive Hypertension in Transgenic Mice Overexpressing Na$^+$–Proton Exchanger", *Circulation Research*, 76, pp. 148–153, Kuro-o et al.

"Blockade of the Na$^+$/H$^+$ Antiport Abolishes Growth Factor–induced DNA Synthesis in Fibroblasts", *The Journal of Biological Chemistry*, 259, pp. 4313–4319, L'Allemain et al.

Copy of the European Search Report dated Mar. 20, 1996.

*Primary Examiner*—Philip I. Datlow
*Attorney, Agent, or Firm*—Merchant, Gould, Smith, Edell, Welter & Schmidt, P.A.

[57] ABSTRACT

A 1,4-benzoxazine derivative of the following formula (I):

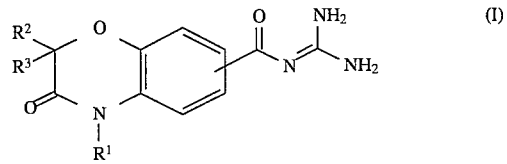

or a pharmaceutically acceptable salt thereof is disclosed. The compound of the present invention is useful as a medicament for preventing or treating disorders induced by intracellular acidosis during myocardial ischemia, such as cardiac dysfunction, myocardial necrosis, arrhythmia, reperfusion injury, and the like, which are observed in ischemic heart diseases (e.g. myocardial infarction, angina pectoris, etc.).

14 Claims, No Drawings

1,4-BENZOXAZINE DERIVATIVE AND PHARMACEUTICAL COMPOSITIONS CONTAINING THE SAME

The present invention relates to a novel 1,4-benzoxazine derivative, a pharmaceutical composition containing the same as an active ingredient and the use thereof. The novel compound of the present invention exhibits an excellent $Na^+/H^+$ exchange inhibitory activity, and hence, is useful as a medicament for treating or preventing disorders caused by intracellular acidosis during myocardial ischemia, such as ischemic heart disease (e.g. myocardial infarction, angina pectoris, etc.), disorders in cardiac function, myocardial necrosis, arrhythmia, reperfusion injury, and the like.

Prior Art

A $Na^+/H^+$ exchange is involved in regulation of pH and sodium ion concentration within cells and of a cellular volume. When the intracellular circumstances are declined to acidosis due to ischemia etc., i.e. the intracellular concentration of hydrogen ion is increased, this exchange mechanism is accelerated, and as a result, excess influx of sodium ion into cells occurs. The resulting difference of osmotic pressure between the inside and the outside of cells then induces influx of water into cells, leading to an increase in cellular volume, i.e. an onset of edema [Biochimica et Biophysica Acta, 988, 73–97 (1989)]. In those cells having the $Na^+/Ca^{2+}$ exchange such as cardiac myocytes, the sodium ions excessively accumulated within cells due to acceleration of the $Na^+/H^+$ exchange are in turn pumped out through the $Na^+/Ca^{2+}$ exchange, and as a result, calcium ions flow into cells. It has been reported that the excess accumulation of calcium ions within cells is a cause of disorders of cardiac function, myocardial necrosis, or arrhythmia [Journal of Cardiovascular Pharmacology, 23, 72–78 (1994)]. Accordingly, those compounds which inhibit the $Na^+/H^+$ exchange are expected to be useful as a medicament for treating or preventing disorders caused by intracellular acidosis during myocardial ischemia, such as cardiac dysfunction, myocardial necrosis, arrhythmia, reperfusion injury, and the like which are usually observed in ischemic heart diseases (e.g. myocardial infarction, angina pectoris, etc.).

It is also known that the $Na^+/H^+$ exchange is deeply involved in cellular growth by a growth factor or hormone stimulation [Biochimica et Biophysica Acta, 988, 73–97 (1989)]. Accordingly, those compounds which inhibit the $Na^+/H^+$ exchange are also expected to be useful as a medicament for treating diseases associated with disorders of cellular growth, for example, restenosis after percutaneous transluminal coronary angioplasty (PTCA).

The acceleration of the $Na^+/H^+$ exchange further induces growth of vascular smooth muscle cells as well as an increase in an amount of body fluid due to decrease in sodium excretion, leading to an onset of hypertension as previously reported [Circulation Research, 76, 148–153 (1995)]. Accordingly, those compounds which inhibit the $Na^+/H^+$ exchange are also expected to be useful as a medicament for treating hypertension.

For the compounds which inhibit the $Na^+/H^+$ exchange, there have been known the amiloride having the following formula (II):

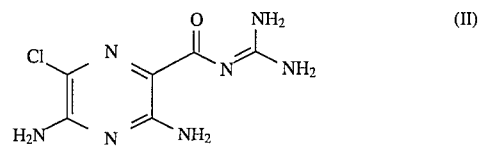

and a derivative thereof, and further benzoylguanidine derivatives, and the like.

The amiloride and a derivative thereof are disclosed in U.S. Pat. No. 3,313,813, The Journal of Biological Chemistry, 259, 4313–4319 (1984), and the benzoylguanidine derivatives are disclosed in U.S. Pat. No. 5,091,394, U.S. Pat No. 5,292,755, EP 556672A, EP 577024A, EP 589336A, EP 604852A, etc.

SUMMARY OF THE INVENTION

Under the circumstances, the present inventors have intensively studied in order to develop a compound having an excellent inhibitory activity against the $Na^+/H^+$ exchange, and as a result, have found that 1,4-benzoxazine derivatives of the formula (I) as shown hereinbelow exhibit an excellent inhibitory activity against the $Na^+/H^+$ exchange.

The object of the present invention is to provide 1,4-benzoxazine derivatives of the following formula (I):

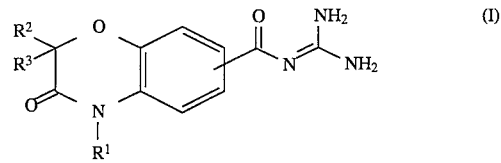

wherein $R^1$ is hydrogen atom, an alkyl group having 1 to 6 carbon atoms or a cycloalkyl group having 5 to 7 carbon atoms; $R^2$ and $R^3$ may be the same or different and are hydrogen atom or an alkyl group having 1 to 4 carbon atoms; the guanidinocarbonyl group bonds at the 6- or 7-position of the benzoxazine ring, or a pharmaceutically acceptable salt thereof.

Another object of the invention is to provide a pharmaceutical composition comprising as an active ingredient the 1,4-benzoxazine derivatives of the formula (I), or a pharmaceutically acceptable salt thereof together with a pharmaceutically acceptable carrier, diluent or vehicle.

Still another object of the invention is to provide the use of the pharmaceutical composition comprising the 1,4-benzoxazine derivatives of the formula (I), or a pharmaceutically acceptable salt thereof as a $Na^+/H^+$ exchange inhibitor.

These and other objects and advantages of the invention will be apparent to those skilled in the art from the following description.

DETAILED DESCRIPTION OF THE INVENTION

The groups in the formula (I) denote as follows.

The alkyl group having 1 to 6 carbon atoms for $R^1$ is a straight chain or branched chain alkyl group having 1 to 6 carbon atoms, such as methyl, ethyl, propyl, 2-propyl, butyl, 2-butyl, pentyl or hexyl. The cycloalkyl group having 5 to 7 carbon atoms for $R^1$ includes, for example, cyclopentyl, cyclohexyl or cycloheptyl. The alkyl group having 1 to 4 carbon atoms for $R^2$ and $R^3$ is a straight chain or branched chain alkyl group having 1 to 4 carbon atoms, such as, methyl, ethyl, propyl, 2-propyl, butyl, etc.

When the $R^2$ and $R^3$ substituents attached at the 2-position of the benzoxazine ring are different from each other, the carbon atom at the 2-position is an asymmetric carbon atom, and hence, there exist stereoisomers (optical isomers). The compounds of the present invention encompass these stereoisomers (optical isomers) as well as a mixture thereof.

Specifically, the compounds (I) of the present invention include the following compounds:

N-Amidino-2,2-dimethyl-4-(2-propyl)-3-oxo-3,4-dihydro-2H-1,4-benzoxazine-7-carboxamide (Example 1);

N-Amidino-2-methyl-4-(2-propyl)-3-oxo-3,4-dihydro-2H-1,4-benzoxazine-7-carboxamide (Example 2);

N-Amidino-4-(2-propyl)-3-oxo-3,4-dihydro-2H-1,4-benzoxazine-7-carboxamide (Example 3);

N-Amidino-4-ethyl-2-methyl-3-oxo-3,4-dihydro-2H-1,4-benzoxazine-7-carboxamide (Example 4);

N-Amidino-2,2-dimethyl-4-(2-propyl)-3-oxo-3,4-dihydro-2H-1,4-benzoxazine-6-carboxamide (Example 5);

N-Amidino-4-ethyl-2-methyl-3-oxo-3,4-dihydro-2H-1,4-benzoxazine-6-carboxamide (Example 6);

N-Amidino-2,2-dimethyl-4-ethyl-3-oxo-3,4-dihydro-2H-1,4-benzoxazine-6-carboxamide (Example 7);

N-Amidino-2-methyl-3-oxo-3,4-dihydro-2H-1,4-benzoxazine-7-carboxamide (Example 8);

N-Amidino-2-ethyl-4-(2-propyl)-3-oxo-3,4-dihydro-2H-1,4-benzoxazine-7-carboxamide (Example 9);

N-Amidino-4-cyclopentyl-2-methyl-3-oxo-3,4-dihydro-2H-1,4-benzoxazine-7-carboxamide (Example 10);

N-Amidino-2-butyl-4-(2-propyl)-3-oxo-3,4-dihydro-2H-1,4-benzoxazine-7-carboxamide (Example 11);

N-Amidino-4-ethyl-3-oxo-3,4-dihydro-2H-1,4-benzoxazine-7-carboxamide (Example 12);

N-Amidino-2,4-diethyl-3-oxo-3,4-dihydro-2H-1,4-benzoxazine-7-carboxamide (Example 13);

(S)-N-Amidino-2-ethyl-4-(2-propyl)-3-oxo-3,4-dihydro-2H-1,4-benzoxazine-7-carboxamide (Example 14);

(R)-N-Amidino-2-ethyl-4-(2-propyl)-3-oxo-3,4-dihydro-2H-1,4-benzoxazine-7-carboxamide (Example 15);

(S)-N-Amidino-2,4-diethyl-3-oxo-3,4-dihydro-2H-1,4-benzoxazine-7-carboxamide (Example 16); and (R)-N-Amidino-2,4-diethyl-3-oxo-3,4-dihydro-2H-1,4-benzoxazine-7-carboxamide (Example 17), or a pharmaceutically acceptable salt thereof.

A pharmaceutically acceptable salt of the compound (I) of the present invention includes a salt with an inorganic acid such as hydrochloric acid, hydrobromic acid, nitric acid, sulfuric acid, phosphoric acid, carbonic acid, etc. or a salt with an organic acid such as acetic acid, lactic acid, citric acid, tartaric acid, methanesulfonic acid, p-toluenesulfonic acid, etc.

Among the above-mentioned compounds, preferred compounds are:

N-Amidino-2,2-dimethyl-4-(2-propyl)-3-oxo-3,4-dihydro-2H-1,4-benzoxazine-6-carboxamide (Example 5);

(S)-N-Amidino-2-ethyl-4-(2-propyl)-3-oxo-3,4-dihydro-2H-1,4-benzoxazine-7-carboxamide (Example 14);

(R)-N-Amidino-2-ethyl-4-(2-propyl)-3-oxo-3,4-dihydro-2H-1,4-benzoxazine-7-carboxamide (Example 15);

(S)-N-Amidino-2,4-diethyl-3-oxo-3,4-dihydro-2H-1,4-benzoxazine-7-carboxamide (Example 16); and (R)-N-Amidino-2,4-diethyl-3-oxo-3,4-dihydro-2H-1,4-benzoxazine-7-carboxamide (Example 17), or a pharmaceutically acceptable salt thereof, for example, a hydrochloride or methanesulfonate.

The compound (I) of the present invention and a pharmaceutically acceptable salt thereof can be prepared, for example, in accordance with the following reaction scheme A:

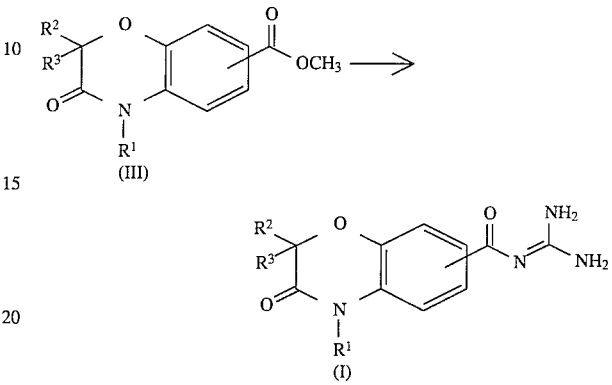

wherein $R^1$, $R^2$ and $R^3$ are as defined above; the methoxycarbonyl group and the guanidinocarbonyl group bonds at the 6- or 7-position of the benzoxazine ring.

The compound (I) of the present invention can be prepared by reacting the ester compound (III) with guanidine. The reaction is carried out in an inert organic solvent at a temperature ranging from ice-cooling to a boiling point of the solvent for 1 to 24 hours using 1 to 20 equivalents of guanidine to the compound (III).

The inert organic solvent used in the reaction includes, for example, methanol, dioxane, tetrahydrofuran, 1,2-dimethoxyethane, dimethylsulfoxide, and the like, or an appropriate mixture of these solvents.

Guanidine may be used in the form of a free base in the reaction scheme A which is prepared by converting a salt of guanidine such as guanidine hydrochloride into a free guanidine with a base such as sodium methoxide or sodium hydride.

An optically active form of the compound (I) of the present invention can be isolated and purified in a usual manner from a mixture of stereoisomers of the compound (I) prepared in the reaction scheme A.

A pharmaceutically acceptable salt of the compound (I) of the present invention can be prepared by reacting the compound (I) prepared in the reaction with the above-mentioned inorganic or organic acid in a usual manner.

The starting compound (III) in the reaction scheme A, i.e. the compound (IIIa) wherein $R^1$ is hydrogen and the compound (IIIb) wherein $R^1$ is an alkyl having 1 to 6 carbon atoms or a cycloalkyl having 5 to 7 carbon atoms, can be prepared in accordance with the following reaction scheme:

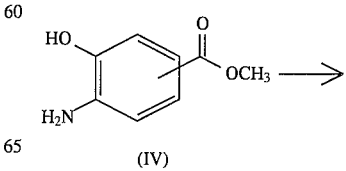

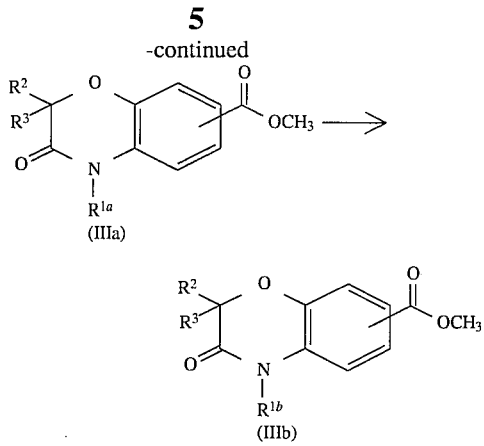

wherein $R^{1a}$ hydrogen atom, $R^{1b}$ is an alkyl having 1 to 6 carbon atoms or a cycloalkyl having 5 to 7 carbon atoms, $R^2$ and $R^3$ are as defined above, and the methoxycarbonyl group bonds at the 4- or 5-position of the benzene ring for the compound (IV) or at the 6- or 7-position for the compounds (IIIa) and (IIIb).

That is, the compound (IIIa) can be prepared by reacting the o-aminophenol derivative (IV) with α-halocarboxylic acid halide having the formula (VII): $(R^2)(R^3)$ CX-COX wherein $R^2$ and $R^3$ are as defined above, X is a halogen atom such as Cl, Br, etc. in the presence of a base to give an amide and cyclizing the resulting amide in the presence of a base.

The reaction of the o-aminophenol with the α-halocarboxylic acid halide can proceed without isolating the intermediate amide.

The α-halocarboxylic acid halide can be prepared from the corresponding α-halocarboxylic acid by reacting the acid with a halogenating agent such as thionyl chloride in a usual manner.

The compound (IIIb) wherein $R^1$ is an alkyl having 1 to 6 carbon atoms or a cycloalkyl having 5 to 7 carbon atoms can be prepared from the compound (IIIa) wherein $R^1$ is hydrogen atom prepared in the above reaction scheme by N-alkylating the compound (IIIa) with an alkyl halide in an inert organic solvent such as dimethylformamide in the presence of a base such as sodium hydride.

Alternatively, the compound (I) of the present invention can be prepared by the following reaction scheme B:

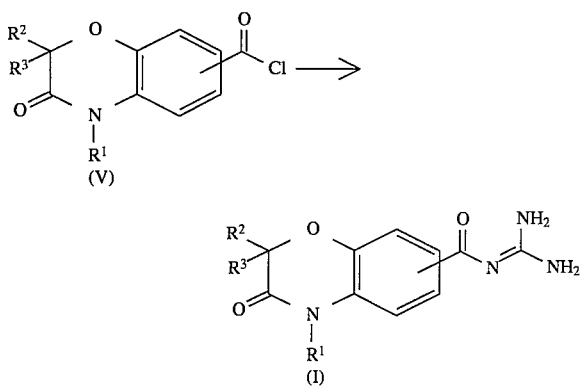

wherein $R^1$, $R^2$ and $R^3$ are as defined above, and the chlorocarbonyl or the guanidinocarbonyl group bonds at the 6- or 7-position of the benzoxazine ring.

An optically active form of the compound (I) and a pharmaceutically acceptable salt thereof is preferably prepared in accordance with the reaction scheme B.

The optically active form of the compound (I) can be prepared in the following manner.

That is, the optically active form of the compound (I) of the present invention can be prepared by reacting the optically active form of the compound (V) with guanidine. This reaction is carried out in an inert organic solvent at a temperature ranging from ice-cooling to a room temperature for 1 to 24 hours using 1 to 20 equivalents of guanidine to the optically active form of the compound (V).

The inert organic solvent used in the reaction includes, for example, dioxane, tetrahydrofuran, 1,2-dimethoxyethane, dimethylsulfoxide, and the like, or an appropriate mixture of these solvents.

Guanidine is used in the form of a free base in the reaction scheme B which is prepared by converting a salt of guanidine into a free guanidine as in the reaction scheme A.

A pharmaceutically acceptable salt of the optically active form of the compound (I) can be prepared by reacting the optically active form of the compound (I) with the above-mentioned inorganic or organic acid in the usual manner.

The starting optically active compound (V) can be prepared in accordance with the following reaction scheme:

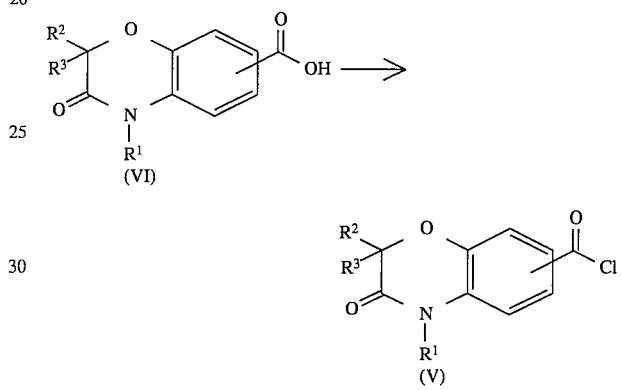

wherein $R^1$, $R^2$ and $R^3$ are as defined above provided that $R^2$ and $R^3$ are different from each other, and the carboxyl and chlorocarbonyl group bond at the 6- or 7-position of the benzoxazine ring.

That is, the optically active compound (V) can be prepared by reacting an optically active compound (VI) with a chlorinating agent such as thionyl chloride in a usual manner.

The optically active compound (VI) can be prepared by first preparing the optically active form of the compound (IIIa) or (IIIb) in the same manner as in the preparation of the starting compound in the reaction scheme A using the optically active form of the α-halocarboxylic acid halide (VII), and then hydrolyzing the resulting optically active compound with concentrated hydrochloric acid etc. in a usual manner.

The optically active form of the α-halocarboxylic acid halide (VII) can be prepared by reacting the optically active form of the corresponding α-halocarboxylic acid with a halogenating agent such as thionyl chloride in a usual manner.

The compounds (I) and a pharmaceutically acceptable salt thereof of the present invention exhibit an excellent $Na^+/H^+$ exchange inhibitory activity, and hence, are useful as a medicament for treating or preventing disorders caused by intracellular acidosis during myocardial ischemia, such as cardiac dysfunction, myocardial necrosis, arrhythmia, reperfusion injury, and the like which are observed in ischemic heart diseases (e.g. myocardial infarction, angina pectoris, etc.).

The compounds (I) and a pharmaceutically acceptable salt thereof of the present invention can be administered orally or parenterally to human.

A dosage form for oral administration includes tablets, granules, powders, fine granules, hard capsules, and the like.

The compounds (I) and a pharmaceutically acceptable salt thereof of the present invention can be formulated into these dosage forms in a usual manner. For example, tablets, granules, powders or fine granules can be prepared by mixing the compound (I) or a pharmaceutically acceptable salt thereof with a conventional pharmaceutical carrier or diluent such as lactose, corn starch, crystalline cellulose, magnesium stearate, hydroxypropylcellulose, talc, and the like. The hard capsules can be prepared by filling an appropriate capsule with the thus prepared fine granules or powders.

A dosage form for parenteral administration includes injections and the like, and can be prepared in a usual manner. For example, the injections can be prepared by dissolving or emulsifying the compound (I) or a pharmaceutically acceptable salt thereof in a purified water for injections, a physiological saline or a fatty vehicle such as vegetable oil, oil emulsion, glycol, and then entering the resulting solution or emulsion into an ampule or a vial under sterilizing conditions.

A dose of the compound (I) of the present invention may vary depending on a severity of disease, conditions, age or weight of patients, or an administration route, but is usually in a range from 0.3 to 600 mg/day for adult with a single or multiple dose for 2 to 3 times a day.

As is shown in Experiments hereinafter, the compounds (I) and a pharmaceutically acceptable salt thereof of the present invention exhibit an excellent $Na^+/H^+$ exchange inhibitory activity, and hence, show an inhibitory activity against reperfusion arrhythmia after myocardial ischemia and an activity to reduce myocardial infarction lesion. In addition, the compounds (I) of the present invention advantageously exhibit a low toxicity. That is, no toxicity was found when each 50 mg/kg of the compounds of Examples 5, 18 and 20 are administered to tail vein of Fischer rats (5 weeks old; each 2 males and females for each group) by a single dose.

Accordingly, a pharmaceutical composition comprising as an active ingredient the compound (I) and a pharmaceutically acceptable salt thereof of the present invention is useful for treating or preventing disorders caused by intracellular acidosis during myocardial ischemia, such as cardiac dysfunction, myocardial necrosis, arrhythmia, reperfusion injury, and the like which are observed in ischemic heart diseases (e.g. myocardial infarction, angina pectoris, etc.).

The present invention is illustrated in more detail by means of the following Preparations, Examples and Experiments but should not be construed to be limited thereto.

In Preparations and Examples, NMR spectrum were obtained by using Hitachi R-24B (60 MHz), Bruker DPX-250 (250 MHz) or Bruker AM-300 (300 MHz).

Preparation 1

Preparation of 7-methoxycarbonyl-2-methyl-3-oxo-3,4-dihydro-2H-1,4-benzoxazine [the compound (IIIa) wherein $R^{1a}$ is hydrogen, either one of $R^2$ and $R^3$ is hydrogen atom and the other is methyl, and methoxycarbonyl group bonds at the 7-position of the benzoxazine ring]:

To a solution of 2-amino-5-methoxycarbonylphenol [Tetrahedron, 46(15), 5177–5186 (1990)] (8.3 g) in dimethylformamide (65 ml) were added potassium carbonate (20.5 g) and 2-chloropropionyl chloride (6.9 g) and the mixture was stirred at room temperature for a day. The reaction solution was poured into water to give precipitates, which were taken by filtration and dried to give 7-methoxycarbonyl-2-methyl-3-oxo-3,4-dihydro-2H-1,4-benzoxazine (7.78 g).

NMR (60 MHz, $CDCl_3$) δ: 1.62 (3H, d, J=7 Hz), 3.92 (3H, s), 4.72 (1H, q, J=7 Hz), 6.90 (1H, d, J=7 Hz), 7.63 (1H, d, J=1 Hz), 7.71 (1H, dd, J=7 Hz, 1 Hz), 9.40–9.62 (1H, b).

Preparation 2

Preparation of 2,2-dimethyl-7-methoxycarbonyl-4-(2-propyl)-3-oxo-3,4-dihydro-2H-1,4-benzoxazine [the compound (IIIb) wherein $R^{1b}$ is 2-propyl, both $R^2$ and $R^3$ are methyl, and methoxycarbonyl group bonds at the 7-position of the benzoxazine ring]:

(1) To a solution of 2-amino-5-methoxycarbonylphenol [Tetrahedron, 46(15), 5177–5186 (1990)] (9.8 g) in a mixed solvent of ethyl acetate (200 ml) and water (200 ml) were added sodium hydrogen carbonate (7.3 g) and 2-bromoisobutyryl bromide (13.7 g) and the mixture was stirred at room temperature for 10 minutes. The organic layer was separated and the solvent was distilled off under reduced pressure. The resulting residue was dissolved in dimethylformamide (500 ml), to the solution was added potassium carbonate (8.9 g) and the mixture was stirred at room temperature for a day. The reaction solution was poured into water to give precipitates, which were taken by filtration and dried to give 2,2-dimethyl-7-methoxycarbonyl-3-oxo-3,4-dihydro-2H-1,4-benzoxazine (10.8 g).

Melting point: 183°–185° C.

NMR (60 MHz, $CDCl_3$) δ: 1.58 (6H, s), 3.88 (3H, s), 6.88 (1H, d, J=9 Hz), 7.60 (1H, d, J=1 Hz), 7.70 (1H, dd, J=9 Hz, 1 Hz), 9.20–9.60 (1H, b).

(2) To a solution of 2,2-dimethyl-7-methoxycarbonyl-3-oxo-3,4-dihydro-2H-1,4-benzoxazine (10.8 g) in dimethylformamide (200 ml) were added 60% sodium hydride (in oil) (1.9 g) and 2-iodopropane (7.8 g) and the mixture was stirred at 60° C. for 5 hours. Water was added to the reaction solution and extraction with ethyl acetate was conducted. The solvent was distilled off under reduced pressure and the resulting residue was subjected to purification by column chromatography using ethyl acetate/hexane [1:5 (v/v)] to give 2,2-dimethyl-7-methoxycarbonyl-4-(2-propyl)-3-oxo-3,4-dihydro-2H-1,4-benzoxazine (6.1 g).

Melting point: 62°–63° C.

NMR (60 MHz, $CDCl_3$) δ:1.45 (6H, s), 1.60 (6H, d, J=6 Hz), 3.90 (3H, s), 4.50–5.00 (1H, m), 7.15 (1H, d, J=8 Hz), 7.65 (1H, d, J=1 Hz), 7.75 (1H, dd, J=8 Hz, 1 Hz).

Preparation 3

Preparation of 7-methoxycarbonyl-2-methyl-4-(2-propyl)-3-oxo-3,4-dihydro-2H-1,4-benzoxazine [the compound (IIIb) wherein $R^{1b}$ is 2-propyl, either one of $R^2$ and $R^3$ is hydrogen atom and the other is methyl, and methoxycarbonyl group bonds at the 7-position of the benzoxazine ring]:

To a solution of 7-methoxycarbonyl-2-methyl-3-oxo-3,4-dihydro-2H-1,4-benzoxazine (prepared in Preparation 1) (6.1 g) in dimethylformamide (120 ml) were added 60% sodium hydride (in oil) (1.1 g) and 2-iodopropane (4.3 g) and the mixture was stirred at 60° C. for 5 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 7-methoxycarbonyl-2-methyl-4-(2-propyl)-3-oxo-3,4-dihydro-2H-1,4-benzoxazine (3.1 g).

NMR (60 MHz, CDCl₃) δ: 1.52 (9H, d, J=7 Hz), 3.82 (3H, s), 4.30–5.00 (2H, m), 7.10 (1H, d, J=9 Hz), 7.60 (1H, d, J=1 Hz), 7.65 (1H, dd, J=9 Hz, 1 Hz).

Preparation 4

Preparation of 7-methoxycarbonyl-4-(2-propyl)-3-oxo-3,4-dihydro-2H-1,4-benzoxazine [the compound (IIIb) wherein $R^{1b}$ is 2-propyl, both $R^2$ and $R^3$ are hydrogen atom, and methoxycarbonyl group bonds at the 7-position of the benzoxazine ring]:

(1) To a solution of 2-amino-5-methoxycarbonylphenol [Tetrahedron, 46(15), 5177–5186 (1990)] (2.20 g) in dimethylformamide (30 ml) were added potassium carbonate (4.00 g) and 2-chloroacetyl chloride (1.50 g) and the mixture was stirred at room temperature for 1 hour. The reaction solution was poured into water to give precipitates, which were taken by filtration and dried to give 7-methoxycarbonyl-3-oxo-3,4-dihydro-2H-1,4-benzoxazine (2.00 g).

Melting point: 258°–260° C.

NMR (60 MHz, DMSO-d₆) δ: 3.85 (3H, s), 4.60 (2H, s), 6.98 (1H, d, J=8 Hz), 7.52 (1H, d, J=1 Hz), 7.60 (1H, dd, J=8 Hz, 1 Hz), 10.70–10.90 (1H, b).

(2) To a solution of 7-methoxycarbonyl-3-oxo-3,4-dihydro-2H-1,4-benzoxazine (1.00 g) in dimethylformamide (10 ml) were added 60% sodium hydride (in oil) (0.25 g) and 2-iodopropane (1.00 g) and the mixture was stirred at room temperature for a day. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 7-methoxycarbonyl-4-(2-propyl)-3-oxo-3,4-dihydro-2H-1,4-benzoxazine (0.30 g).

NMR (60 MHz, CDCl₃) δ: 1.60 (6H, d, J=7 Hz), 3.90 (3H, s), 4.53 (2H, s), 4.52–5.00 (1H, m), 7.18 (1H, d, J=8 Hz), 7.66 (1H, d, J=1 Hz), 7.70 (1H, dd, J=8 Hz, 1 Hz).

Preparation 5

Preparation of 4-ethyl-7-methoxycarbonyl-2-methyl-3-oxo-3,4-dihydro-2H-1,4-benzoxazine [the compound (IIIb) wherein $R^{1b}$ is ethyl, either one of $R^2$ and $R^3$ is hydrogen atom and the other is methyl, and methoxycarbonyl group bonds at the 7-position of the benzoxazine ring]:

To a solution of 7-methoxycarbonyl-2-methyl-3-oxo-3,4-dihydro-2H-1,4-benzoxazine (prepared in Preparation 1) (1.00 g) in dimethylformamide (5 ml) were added 60% sodium hydride (in oil) (0.22 g) and ethyl iodide (0.78 g) and the mixture was stirred at room temperature for 3 hours. Water was added to the reaction solution and extraction with ethyl acetate was conducted. The solvent was distilled off under reduced pressure to give 4-ethyl-7-methoxycarbonyl-2-methyl-3-oxo-3,4-dihydro-2H-1,4-benzoxazine (0.89 g).

Melting point: 68°–69° C.

NMR (60 MHz, CDCl₃) δ: 1.25 (3H, t, J=8 Hz), 1.55 (3H, d, J=7 Hz), 3.86 (3H, s), 3.70–4.20 (2H, m), 4.60 (1H, q, J=7 Hz), 7.01 (1H, d, J=8 Hz), 7.60 (1H, d, J=1 Hz), 7.70 (1H, dd, J=8 Hz, 1 Hz).

Preparation 6

Preparation of 2,2-dimethyl-6-methoxycarbonyl-4-(2-propyl)-3-oxo-3,4-dihydro-2H-1,4-benzoxazine [the compound (IIIb) wherein $R^{1b}$ is 2-propyl, both $R^2$ and $R^3$ are methyl, and methoxycarbonyl group bonds at the 6-position of the benzoxazine ring]:

(1) To solution of 2-amino-4-methoxycarbonylphenol [Acta Chimica Academiae Scientiarum Hungaricae, 99 (1), 49–50 (1979)] (4.78 g) in a mixed solvent of ethyl acetate (50 ml) and water (50 ml) were added sodium hydrogen carbonate (3.6 g) and 2-bromoisobutyryl bromide (6.90 g) and the mixture was stirred at room temperature for 10 minutes. The organic layer was separated and the solvent was distilled off under reduced pressure. The resulting residue was dissolved in dimethylformamide (70 ml), to the solution was added potassium carbonate (4.35 g) and the mixture was stirred at room temperature for a day. The reaction solution was poured into water to give precipitates, which were taken by filtration and dried to give 2,2-dimethyl-6-methoxycarbonyl-3-oxo-3,4-dihydro-2H-1,4-benzoxazine (5.4 g).

Melting point: 199°–200° C. 0

NMR (60 MHz, DMSO-d₆) δ: 1.50 (6H, s), 3.75 (3H, s), 6.96 (1H, d, J=8 Hz), 7.50 (1H, d, J=1 Hz), 7.60 (1H, dd, J=8 Hz, 1 Hz), 10.40–10.70 (1H, b).

(2) To a solution of 2,2-dimethyl-6-methoxycarbonyl-3-oxo-3,4-dihydro-2H-1,4-benzoxazine (3.0 g) in dimethylformamide (60 ml) were added 60% sodium hydride (in oil) (0.61 g) and 2-iodopropane (2.38 g) and the mixture was stirred at 60° C. for 2 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 2,2-dimethyl-6-methoxycarbonyl-4-(2-propyl)-3-oxo-3,4-dihydro-2H-1,4-benzoxazine (1.1 g).

Melting point: 75°–77° C.

NMR (60 MHz, CDCl₃) δ:1.50 (6H, s), 1.60 (6H, d, J=6 Hz), 3.98 (3H, s), 4.50–5.10 (1H, m), 7.06 (1H, d, J=7 Hz), 7.82 (1H, dd, J=7 Hz, 1 Hz), 7.87 (1H, d, J=1 Hz).

Preparation 7

Preparation of 4-ethyl-6-methoxycarbonyl-2-methyl-3-oxo-3,4-dihydro-2H-1,4-benzoxazine [the compound (IIIb) wherein $R^{1b}$ is ethyl, either one of $R^2$ and $R^3$ is hydrogen atom and the other is methyl, and methoxycarbonyl group bonds at the 6-position of the benzoxazine ring]:

(1) To a solution of 2-amino-4-methoxycarbonylphenol [Acta Chimica Academiae Scientiarum Hungaricae, 99(1), 49–50 (1979)] (5.0 g) in dimethylformamide (30 ml) were added potassium carbonate (8.3 g) and 2-chloropropionyl chloride (4.0 g) and the mixture was stirred at 50° C. for 2 hours. Water was added to the reaction solution and extraction with ethyl acetate was conducted. The extraction was concentrated and hexane was added thereto to give precipitates, which were taken by filtration and dried to give 6-methoxycarbonyl-2-methyl-3-oxo-3,4-dihydro-2H-1,4-benzoxazine (4.7 g).

Melting point: 156°–159° C.

NMR (60 MHz, CDCl₃) δ: 1.65 (3H, d, J=6 Hz), 3.85 (3H, s), 4.68 (1H, q, J=6 Hz), 6.98 (1H, d, J=8 Hz), 7.61 (1H, d, J=1 Hz), 7.72 (1H, dd, J=8 Hz, 1 Hz).

(2) To a solution of 6-methoxycarbonyl-2-methyl-3-oxo-3,4-dihydro-2H-1,4-benzoxazine (2.2 g) in dimethylformamide (20 ml) were added 60% sodium hydride (in oil) (0.5 g) and ethyl iodide (1.8 g) and the mixture was stirred at room temperature for a day. Water was added to the reaction solution and extraction with ethyl acetate was conducted.

The solvent was distilled off under reduced pressure and the resulting residue was subjected to purification by column chromatography using ethyl acetate/hexane [1:1 (v/v)] to give 4-ethyl-6-methoxycarbonyl-2-methyl-3-oxo-3,4-dihydro-2H-1,4-benzoxazine (2.0 g).

NMR (60 MHz, CDCl$_3$) δ: 1.29 (3H, t, J=8 Hz), 1.59 (3H, d, J=7 Hz), 3.92 (3H, s), 4.08 (2H, q, J=8 Hz), 4.74 (1H, q, J=7 Hz), 7.04 (1H, d, J=8 Hz), 7.70 (1H, d, J=1 Hz), 7.85 (1H, dd, J=8 Hz, 1 Hz).

Preparation 8

Preparation of 2,2-dimethyl-4-ethyl-6-methoxycarbonyl-3-oxo-3,4-dihydro-2H-1,4-benzoxazine [the compound (IIIb) wherein $R^{1b}$ is ethyl, both $R^2$ and $R^3$ are methyl, and methoxycarbonyl group bonds at the 6-position of the benzoxazine ring]:

To a solution of 2,2-dimethyl-6-methoxycarbonyl-3-oxo-3,4-dihydro-2H-1,4-benzoxazine [prepared in Preparation 6(1)] (1.50 g) in dimethylformamide (20 ml) were added 60% sodium hydride (in oil) (0.3 g) and ethyl iodide (1.1 g) and the mixture was stirred at 50° C. for 1 hour. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 2,2-dimethyl-4-ethyl-6-methoxycarbonyl-3-oxo-3,4-dihydro-2H-1,4-benzoxazine (1.6 g).

Melting point: 76°–78° C.

NMR (60 MHz, CDCl$_3$) δ: 1.30 (3H, t, J=6 Hz), 1.53 (6H, s), 3.92 (3H, s), 4.05 (2H, q, J=6 Hz), 7.00 (1H, d, J=9 Hz), 7.68 (1H, d, J=1 Hz), 7.75 (1H, dd, J=9 Hz, 1 Hz).

Preparation 9

Preparation of 2-ethyl-7-methoxycarbonyl-4-(2-propyl)-3-oxo-3,4-dihydro-2H-1,4-benzoxazine [the compound (IIIb) wherein $R^{1b}$ is 2-propyl, either one of $R^2$ and $R^3$ is hydrogen atom and the other is ethyl, and methoxycarbonyl group bonds at the 7-position of the benzoxazine ring]:

(1) To a solution of 2-amino-5-methoxycarbonylphenol [Tetrahedron, 46(15), 5177–5186 (1990)] (9.80 g) in a mixed solvent of ethyl acetate (200 ml) and water (200 ml) were added sodium hydrogen carbonate (7.30 g) and 2-bromobutyryl bromide (13.70 g) and the mixture was stirred at room temperature for 10 minutes. The organic layer was separated and the solvent was distilled off under reduced pressure. The resulting residue was dissolved in dimethylformamide (500 ml), to the solution was added potassium carbonate (8.90 g) and the mixture was stirred at room temperature for a day. The reaction solution was poured into water to give precipitates, which were taken by filtration and dried to give 2-ethyl-7-methoxycarbonyl-3-oxo-3,4-dihydro-2H-1,4-benzoxazine (12.0 g).

Melting point: 132°–134° C.

NMR (60 MHz, CDCl$_3$) δ: 1.10 (3H, t, J=7 Hz), 1.70–2.30 (2H, m), 3.90 (3H, s), 4.50 (1H, t, J=6 Hz), 6.86 (1H, d, J=7 Hz), 7.60 (1H, d, J=1 Hz), 7.66 (1H, dd, J=7 Hz, 1 Hz).

(2) To a solution of 2-ethyl-7-methoxycarbonyl-3-oxo-3,4-dihydro-2H-1,4-benzoxazine (10.00 g) in dimethylformamide (200 ml) were added 60% sodium hydride (in oil) (1.87 g) and 2-iodopropane (7.80 g) and the mixture was stirred at 60° C. for 2 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 2-ethyl-7-methoxycarbonyl-4-(2-propyl)-3-oxo-3,4-dihydro-2H-1,4-benzoxazine (4.43 g).

NMR (60 MHz, CDCl$_3$) δ: 1.02 (3H, t, J=7 Hz), 1.52 (6H, d, J=6 Hz), 1.60–2.20 (2H, m), 3.90 (3H, s), 4.37 (1H, dd, J=8 Hz, 5 Hz), 4.50–5.00 (1H, m), 7.18 (1H, d, J=9 Hz), 7.65 (1H, d, J=1 Hz), 7.78 (1H, dd, J=9 Hz, 1 Hz).

Preparation 10

Preparation of 4-cyclopentyl-7-methoxycarbonyl-2-methyl-3-oxo-3,4-dihydro-2H-1,4-benzoxazine [the compound (IIIb) wherein $R^{1b}$ is cyclopentyl, either one of $R^2$ and $R^3$ is hydrogen atom and the other is methyl, and methoxycarbonyl group bonds at the 7-position of the benzoxazine ring]:

To a solution of 7-methoxycarbonyl-2-methyl-3-oxo-3,4-dihydro-2H-1,4-benzoxazine (prepared in Preparation 1) (4.0 g) in dimethylformamide (80 ml) were added 60% sodium hydride (in oil) (0.73 g) and cyclopentyl bromide (2.5 g) and the mixture was stirred at 70° C. for a day. Water was added to the reaction solution and extraction with ethyl acetate was conducted. The solvent was distilled off under reduced pressure and the resulting residue was subjected to purification by column chromatography using chloroform to give 4-cyclopentyl-7-methoxycarbonyl-2-methyl-3-oxo-3,4-dihydro-2H-1,4-benzoxazine (2.5 g) as an oil.

NMR (60 MHz, CDCl$_3$) δ: 1.55 (3H, d, J=6 Hz), 1.40–2.50 (8H, m), 3.95 (3H, s), 4.30–5.10 (2H, m), 7.16 (1H, d, J=8 Hz), 7.72 (1H, d, J=1 Hz), 7.84 (1H, dd, J=8 Hz, 1 Hz).

Preparation 11

Preparation of 2-butyl-7-methoxycarbonyl-4-(2-propyl)-3-oxo-3,4-dihydro-2H-1,4-benzoxazine [the compound (IIIb) wherein $R^{1b}$ is 2-propyl, either one of $R^2$ and $R^3$ is hydrogen atom and the other is butyl, and methoxycarbonyl group bonds at the 7-position of the benzoxazine ring]:

(1) To a solution of 2-amino-5-methoxycarbonylphenol [Tetrahedron, 4.6 (15), 5177–5186 (1990)] (8.0 g) in a mixed solvent of ethyl acetate (200 ml) and water (200 ml) were added sodium hydrogen carbonate (11.18 g) and 2-bromohexanoyl bromide (12.73 g) and the mixture was stirred at room temperature for 10 minutes. The organic layer was separated and the solvent was distilled off under reduced pressure. The resulting residue was dissolved in dimethylformamide (300 ml), to the solution was added potassium carbonate (6.0 g) and the mixture was stirred at room temperature for 1 hour. Water was added to the reaction solution and extraction with ethyl acetate was conducted. The solvent was distilled off under reduced pressure and the resulting crystals were recrystallized from ether to give 2-butyl-7-methoxycarbonyl-3-oxo-3,4-dihydro-2H-1,4-benzoxazine (10.3 g).

Melting point: 139°–140° C.

NMR (60 MHz, CDCl$_3$) δ: 0.70–1.10 (3H, m), 1.20–2.10 (6H, m), 3.88 (3H, s), 4.65 (1H, t, J=7 Hz), 6.90 (1H, d, J=9 Hz), 7.60 (1H, dd, J=9 Hz, 1 Hz), 7.80 (1H, d, J=1 Hz), 9.50–9.70 (1H, b).

(2) To a solution of 2-butyl-7-methoxycarbonyl-3-oxo-3,4-dihydro-2H-1,4-benzoxazine (9.0 g) in dimethylformamide (180 ml) were added 60% sodium hydride (in oil) (1.63 g) and 2-iodopropane (6.35 g) and the mixture was stirred at 80° C. for 2 hours. Water was added to the reaction solution and extraction with ethyl acetate was conducted. The solvent was distilled off under reduced pressure and the resulting residue was subjected to purification by column chromatography using ethyl acetate/hexane [1:8 (v/v)] to give 2-butyl-7-methoxycarbonyl-4-(2-propyl)-3-oxo-3,4-dihydro-2H-1,4-benzoxazine (2.2 g) as an oil.

NMR (60 MHz, CDCl$_3$) δ: 0.70–1.10 (3H, m), 1.20–2.10 (6H, m), 1.50 (6H, d, J=6 Hz), 3.90 (3H, s), 4.30–5.10 (2H, m), 7.13 (1H, d, J=8 Hz), 7.70 (1H, dd, J=8 Hz, 1 Hz), 7.75 (1H, d, J=1 Hz).

Preparation 12

Preparation of 4-ethyl-7-methoxycarbonyl-3-oxo-3,4-dihydro-2H-1,4-benzoxazine [the compound (IIIb) wherein $R^{1b}$ is ethyl, both $R^2$ and $R^3$ are hydrogen atom, and methoxycarbonyl group bonds at the 7-position of the benzoxazine ring]:

To a solution of 7-methoxycarbonyl-3-oxo-3,4-dihydro-2H-1,4-benzoxazine [prepared in Preparation 4(1)] (1.0 g) in dimethylformamide (80 ml) were added 60% sodium hydride (in oil) (0.25 g) and ethyl iodide (1.0 g) and the mixture was stirred at room temperature for a day. Water was added to the reaction solution and extraction with ethyl acetate was conducted. The solvent was distilled off under reduced pressure and the resulting residue was recrystallized from ethyl acetate/hexane to give 4-ethyl-7-methoxycarbonyl-3-oxo-3,4-dihydro-2H-1,4-benzoxazine (0.3 g).

NMR (60 MHz, CDCl$_3$) δ: 1.30 (3H, t, J=6 Hz), 3.90 (3H, s), 4.05 (2H, q, J=6 Hz), 4.65 (2H, s), 7.02 (1H, d, J=7 Hz), 7.60 (1H, d, J=1 Hz), 7.74 (1H, dd, J=7 Hz, 1 Hz).

Preparation 13

Preparation of 2,4-diethyl-7-methoxycarbonyl-3-oxo-3,4-dihydro-2H-1,4-benzoxazine [the compound (IIIb) wherein $R^{1b}$ is ethyl, either one of $R^2$ and $R^3$ is hydrogen atom and the other is ethyl, and methoxycarbonyl group bonds at the 7-position of the benzoxazine ring]:

To a solution of 2-ethyl-7-methoxycarbonyl-3-oxo-3,4-dihydro-2-H-1,4-benzoxazine [prepared in Preparation 9(1)] (6.0 g) in dimethylformamide (60 ml) were added 60% sodium hydride (in oil) (1.02 g) and ethyl iodide (4.37 g) and the mixture was stirred at room temperature for 2 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give 2,4-diethyl-7-methoxycarbonyl-3-oxo-3,4-dihydro-2H-1,4-benzoxazine (6.0 g).

Melting point: 64°–65° C.

NMR (60 MHz, CDCl$_3$) δ: 1.10 (3H, t, J=7 Hz), 1.30 (3H, t, J=6 Hz), 1.60–2.10 (2H, m), 3.95 (3H, s), 3.80–4.05 (2H, m), 4.55 (1H, dd, J=7 Hz, 5 Hz), 7.02 (1H, d, J=7 Hz), 7.69 (1H, d, J=1 Hz), 7.80 (1H, dd, J=7 Hz, 1 Hz).

Preparation 14

Preparation of (S)-2-ethyl-4-(2-propyl)-3-oxo-3,4-dihydro-2H-1,4-benzoxazine-7-carbonyl chloride [(S)-form of the compound (V) wherein $R^1$ is 2-propyl, either one of $R^2$ and $R^3$ is hydrogen atom and the other is ethyl, and chlorocarbonyl group bonds at the 7-position of the benzoxazine ring]:

(1) A solution of (R)-2-chlorobutyric acid [Bulletin de la Societe Chimique de Belgique, 42, 455 (1993)] (7.0 g) in thionyl chloride (45 ml) was stirred for 2 hours under reflux. The reaction solution was concentrated under reduced pressure to give (R)-2-chlorobutyryl chloride (7.5 g) as an oil.

NMR (60 MHz, CDCl$_3$) δ: 1.10 (3H, t, J=6 Hz), 1.80–2.50 (2H, m), 4.50 (1H, t, J=6 Hz).

(2) To a solution of 2-amino-5-methoxycarbonylphenol [Tetrahedron, 46(15), 5177–5186 (1990)] (7.50 g) in a mixed solvent of ethyl acetate (60 ml) and water (60 ml) were added sodium hydrogen carbonate (5.20 g) and (R)-2-chlorobutyryl chloride (7.50 g) and the mixture was stirred at room temperature for 10 minutes. The organic layer was separated and the solvent was distilled off under reduced pressure. The resulting residue was dissolved in dimethylformamide (90 ml), to the solution was added potassium carbonate (6.20 g) and the mixture was stirred at room temperature overnight. Water was added to the reaction solution and the resulting crystals were taken by filtration to give (S)-2-ethyl-7-methoxycarbonyl-3-oxo-3,4-dihydro-2H-1,4-benzoxazine (9.38 g).

NMR (60 MHz, CDCl$_3$) δ: 1.10 (3H, t, J=7 Hz), 1.70–2.30 (2H, m), 3.90 (3H, s), 4.50 (1H, t, J=7 Hz), 6.86 (1H, d, J=7 Hz), 7.60 (1H, d, J=1 Hz), 7.66 (1H, dd, J=7 Hz, 1 Hz), 9.50–9.80 (1H, b).

(3) A solution of (S)-2-ethyl-7-methoxycarbonyl-3-oxo-3,4-dihydro-2H-1,4-benzoxazine (1.60 g) in dimethylformamide (50 ml) were added 60% sodium hydride (in oil) (0.27 g) and 2-iodopropane (1.38 g) and the mixture was stirred at 60° C. overnight. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give (S)-2-ethyl-7-methoxycarbonyl-4-(2-propyl)-3-oxo-3,4-dihydro-2H-1,4-benzoxazine (0.85 g) as an oil.

NMR (60 MHz, CDCl$_3$) δ: 1.02 (3H, t, J=7 Hz), 1.52 (6H, d, J=6 Hz), 1.30–2.20 (2H, m), 3.90 (3H, s), 4.20–5.10 (2H, m), 7.18 (1H, d, J=9 Hz), 7.65 (1H, d, J=1 Hz), 7.78 (1H, dd, J=9 Hz, 1 Hz).

(4) A mixture of (S)-2-ethyl-7-methoxycarbonyl-4-(2-propyl)-3-oxo-3,4-dihydro-2H-1,4-benzoxazine (0.85 g) in concentrated hydrochloric acid (20 ml) was stirred under reflux for a day. The concentrated hydrochloric acid was distilled off under reduced pressure. Water was added to the residue and extraction with ethyl acetate was conducted. The extract was washed with water and then the solvent was distilled off under reduced pressure to give (S)-2-ethyl-4-(2-propyl)-3-oxo-3,4-dihydro-2H-1,4-benzoxazine-7-carboxylic acid (0.70 g).

NMR (60 MHz, CDCl$_3$) δ: 1.10 (3H, t, J=6 Hz), 1.60 (6H, d, J=6 Hz), 1.70–2.10 (2H, m), 4.20–5.10 (2H, m), 7.16 (1H, d, J=7 Hz), 7.70 (1H, d, J=1 Hz), 7.78 (1H, dd, J=7 Hz, 1 Hz), 9. 20–9.70 (1H, b).

(5) A mixture of (S)-2-ethyl-4-(2-propyl)-3-oxo-3,4-dihydro-2H-1,4-benzoxazine-7-carboxylic acid (0.70 g) in thionyl chloride (15 ml) was stirred under reflux for 2 hours. Thionyl chloride was distilled off under reduced pressure to give (S)-2-ethyl-4-(2-propyl)-3-oxo-3,4-dihydro-2H-1,4-benzoxazine-7-carbonyl chloride (0.70 g).

Preparation 15

Preparation of (R)-2-ethyl-4-(2-propyl)-3-oxo-3,4-dihydro-2H-1,4-benzoxazine-7-carbonyl chloride [(R)-form of the compound (V) wherein $R^1$ is 2-propyl, either one of $R^2$ and $R^3$ is hydrogen atom and the other is ethyl, and chlorocarbonyl group bonds at the 7-position of the benzoxazine ring]:

(1) A solution of (S)-2-chlorobutyric acid [Bulletin de la Societe Chimique de Belgique, 42, 454 (1993)] (11.4 g) in thionyl chloride (50 ml) was stirred for 2 hours under reflux. The reaction solution was concentrated under reduced pressure to give (S)-2-chlorobutyryl chloride (10.0 g) as an oil.

NMR (60 MHz, CDCl$_3$) δ: 1.10 (3H, t, J=6 Hz), 1.70–2.60 (2H, m), 4.50 (1H, t, J=6 Hz).

(2) To a solution of 2-amino-5-methoxycarbonylphenol [Tetrahedron, 46(15), 5177–5186 (1990)] (5.90 g) in a mixed solvent of ethyl acetate (60 ml) and water (60 ml) were added sodium hydrogen carbonate (5.40 g) and (S)-2-chlorobutyryl chloride (7.00 g) and the mixture was stirred at room temperature for 10 minutes. The organic layer was separated and the solvent was distilled off under reduced pressure. The resulting residue was dissolved in dimethylformamide (70 ml), to the solution was added potassium carbonate (4.90 g) and the mixture was stirred at room temperature overnight. Water was added to the reaction solution and the resulting crystals were taken by filtration to give (R)-2-ethyl-7-methoxycarbonyl-3-oxo-3,4-dihydro-2H-1,4-benzoxazine (6.0 g).

NMR (60 MHz, CDCl$_3$) δ: 1.10 (3H, t, J=7 Hz), 1.60–2.30 (2H, m), 3.90 (3H, s), 4.50 (1H, dd, J=7 Hz, 4 Hz), 6.86 (1H, d, J=7 Hz), 7.60 (1H, d, J=1 Hz), 7.66 (1H, dd, J=7 Hz, 1 Hz), 9.40–9.70 (1H, b).

(3) To a solution of (R)-2-ethyl-7-methoxycarbonyl-3-oxo-3,4-dihydro-2H-1,4-benzoxazine (3.90 g) in dimethylformamide (100 ml) were added 60% sodium hydride (in oil) (0.71 g) and 2-iodopropane (3.0 g) and the mixture was stirred at 60° C. for 3 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give (R)-2-ethyl-7-methoxycarbonyl-4-(2-propyl)-3-oxo-3,4-dihydro-2H-1,4-benzoxazine (1.70 g) as an oil.

NMR (60 MHz, CDCl$_3$) δ: 1.02 (3H, t, J=7 Hz), 1.52 (6H, d, J=6 Hz), 1.40–2.20 (2H, m), 3.89 (3H, s), 4.20–5.10 (2H, m), 7.18 (1H, d, J=7 Hz), 7.65 (1H, s), 7.78 (1H, d, J=7 Hz).

(4) A mixture of (R)-2-ethyl-7-methoxycarbonyl-4-(2-propyl)-3-oxo-3,4-dihydro-2H-1,4-benzoxazine (1.70 g) in concentrated hydrochloric acid (30 ml) was stirred under reflux for a day. The concentrated hydrochloric acid was distilled off under reduced pressure. Water was added to the residue and extraction with ethyl acetate was conducted. The extract was washed with water and then the solvent was distilled off under reduced pressure to give (R)-2-ethyl-4-(2-propyl)-3-oxo-3,4-dihydro-2H-1,4-benzoxazine-7-carboxylic acid (1.60 g).

NMR (250 MHz, CDCl$_3$) δ: 1.07 (3H, t, J=8 Hz), 1.54 (3H, d, J=7 Hz), 1.56 (3H, d, J=7 Hz), 1.70–2.10 (2H, m), 4.40 (1H, dd, J=8 Hz, 5 Hz), 4.60–4.90 (1H, m), 7.18 (1H, d, J=9 Hz), 7.73 (1H, d, J=2 Hz), 7.79 (1H, dd, J=9 Hz, 2 Hz).

(5) A mixture of (R)-2-ethyl-4-(2-propyl)-3-oxo-3,4-dihydro-2H-1,4-benzoxazine-7-carboxylic acid (1.60 g) in thionyl chloride (30 ml) was stirred under reflux for 2 hours. Thionyl chloride was distilled off under reduced pressure to give (R)-2-ethyl-4-(2-propyl)-3-oxo-3,4-dihydro-2H-1,4-benzoxazine-7-carbonyl chloride (1.70 g).

Preparation 16

Preparation of (S)-2,4-diethyl-3-oxo-3,4-dihydro-2H-1,4-benzoxazine-7-carbonyl chloride [(S)-form of the compound (V) wherein R$^1$ is ethyl, either one of R$^2$ and R$^3$ is hydrogen atom and the other is ethyl, and chlorocarbonyl group bonds at the 7-position of the benzoxazine ring]:

(1) To a solution of (S)-2-ethyl-7-methoxycarbonyl-3-oxo-3,4-dihydro-2H-1,4-benzoxazine [prepared in Preparation 14(2)] (2.00 g) in dimethylformamide (20 ml) were added 60% sodium hydride (in oil) (0.37 g) and ethyl iodide (1.90 g) and the mixture was stirred under ice cooling for 2 hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give (S)-2,4-diethyl-7-methoxycarbonyl-3-oxo-3,4-dihydro-2H-1,4-benzoxazine (2.15 g).

NMR (250 MHz, CDCl$_3$) δ: 1.08 (3H, t, J=7 Hz), 1.28 (3H, t, J=7 Hz), 1.76–1.99 (2H, m), 3.91 (3H, s), 4.00 (2H, q, J=7 Hz), 4.50 (1H, dd, J=9 Hz, 5 Hz), 7.00 (1H, d, J=9 Hz), 7.66 (1H, d, J=2 Hz), 7.73 (1H, dd, J=9 Hz, 2 Hz).

(2) A mixture of (S)-2,4-diethyl-7-methoxycarbonyl-3-oxo-3,4-dihydro-2H-1,4-benzoxazine (1.90 g) in concentrated hydrochloric acid (40 ml) was stirred under reflux for a day. The concentrated hydrochloric acid was distilled off under reduced pressure to give (S)-2,4-diethyl-3-oxo-3,4-dihydro-2H-1,4-benzoxazine-7-carboxylic acid (1.47 g).

NMR (250 MHz, CDCl$_3$) δ: 1.09 (3H, t, J=8 Hz), 1.29 (3H, t, J=7 Hz), 1.88–1.99 (2H, m), 4.02 (2H, q, J=7 Hz), 4.53 (1H, dd, J=9 Hz, 5 Hz), 7.04 (1H, d, J=9 Hz), 7.73 (1H, d, J=2 Hz), 7.82 (1H, dd, J=9 Hz, 2 Hz), 8.30–11.0 (1H, b).

(3) A mixture of (S)-2,4-diethyl-3-oxo-3,4-dihydro-2H-1,4-benzoxazine-7-carboxylic acid (1.1 g) in thionyl chloride (15 ml) was stirred under reflux for 2 hours. Thionyl chloride was distilled off under reduced pressure to give (S)-2,4-diethyl-3-oxo-3,4-dihydro-2H-1,4-benzoxazine-7-carbonyl chloride (1.25 g).

Preparation 17

Preparation of (R)-2,4-diethyl-3-oxo-3,4-dihydro-2H-1,4-benzoxazine-7-carbonyl chloride [(R)-form of the compound (V) wherein R$^1$ is ethyl, either one of R$^2$ and R$^3$ is hydrogen atom and the other is ethyl, and chlorocarbonyl group bonds at the 7-position of the benzoxazine ring]:

(1) To a solution of (R)-2-ethyl-7-methoxycarbonyl-3-oxo-3,4-dihydro-2H-1,4-benzoxazine [prepared in Preparation 15(2)] (2.00 g) in dimethylformamide (20 ml) were added 60% sodium hydride (in oil) (0.35 g) and ethyl iodide (1.46 g) and the mixture was stirred at room temperature for two and a half hours. Water was added to the reaction solution and extraction with ethyl acetate was conducted. The solvent was distilled off under reduced pressure and the resulting residue was subjected to purification by column chromatography using ethyl acetate/hexane [1:4 (v/v)] to give (R)-2,4-diethyl-7-methoxycarbonyl-3-oxo-3,4-dihydro-2H-1,4-benzoxazine(2.0g).

NMR (250 MHz, CDCl$_3$) δ: 1.07 (3H, t, J=8 Hz), 1.27 (3H, t, J=7 Hz), 1.70–2.10 (2H, m), 3.91 (3H, s), 4.00 (2H, q, J=7 Hz), 4.59 (1H, dd, J=9 Hz, 5 Hz), 7.00 (1H, d, J=9 Hz), 7.66 (1H, d, J=2 Hz), 7.73 (1H, dd, J=9 Hz, 2 Hz).

(2) A mixture of (R)-2,4-diethyl-7-methoxycarbonyl-3-oxo-3,4-dihydro-2H-1,4-benzoxazine (1.80 g) in concentrated hydrochloric acid (30 ml) was stirred under reflux for a day. The concentrated hydrochloric acid was distilled off under reduced pressure to give (R)-2,4-diethyl-3-oxo-3,4-dihydro-2H-1,4-benzoxazine-7-carboxylic acid (1.20 g).

NMR (250 MHz, CDCl$_3$) δ: 1.09 (3H, t, J=8 Hz), 1.29 (3H, t, J=7 Hz), 1.70–2.10 (2H, m), 4.02 (2H, q, J=7 Hz), 4.52 (1H, dd, J=9 Hz, 5 Hz), 7.04 (1H, d, J=9 Hz), 7.73 (1H, d, J=2 Hz), 7.81 (1H, dd, J=9 Hz, 2 Hz), 8.10–10.00 (1H, b).

(3) A mixture of (R)-2,4-diethyl-3-oxo-3,4-dihydro-2H-1,4-benzoxazine-7-carboxylic acid (1.0 g) in thionyl chloride (10 ml) was stirred under reflux for 2 hours. Thionyl chloride was distilled off under reduced pressure to give (R)-2,4-diethyl-3-oxo-3,4-dihydro-2H-1,4-benzoxazine-7-carbonyl chloride (1.14 g).

EXAMPLE 1

Preparation of N-amidino-2,2-dimethyl-4-(2-propyl)-3-oxo-3,4-dihydro-2H-1,4-benzoxazine-7-carboxamide [the compound (I) wherein $R^1$ is 2-propyl, both $R^2$ and $R^3$ are methyl, and guanidinocarbonyl group bonds at the 7-position of the benzoxazine ring]:

Guanidine hydrochloride (7.50 g) was added to a solution of sodium methoxide in methanol prepared from sodium (1.83 g) and methanol (35 ml). The mixture was stirred under reflux for 30 minutes and then filtered while heating. To the filtrate was added 2,2-dimethyl-7-methoxycarbonyl-4-(2-propyl)-3-oxo-3,4-dihydro-2H-1,4-benzoxazine (prepared in Preparation 2) (2.50 g) and the mixture was stirred under reflux for 3 hours. After concentrating the reaction mixture, water was added and extraction with ethyl acetate was conducted. The solvent was distilled off under reduced pressure and the obtained crystals were recrystallized from acetonitrile to give the title compound (0.40 g) as a colorless product.

Melting point: 230°–231° C.

NMR (60 MHz, DMSO-$d_6$) δ: 1.33 (6H, s), 1.49 (6H, d, J=6 Hz), 4.50–4.90 (1H, m), 7.30 (1H, d, J=7 Hz), 7.60–7.95 (6H, b).

Elementary Analysis for $C_{15}H_{20}N_4O_3$: Calculated (%): C,59.20; H,6.62; N,18.41 Found (%): C,59.00; H,6.60; N,18.64

EXAMPLE 2

Preparation of N-amidino-2-methyl-4-(2-propyl)-3-oxo-3,4-dihydro-2H-1,4-benzoxazine-7-carboxamide [the compound (I) wherein $R^1$ is 2-propyl, either one of $R^2$ and $R^3$ is hydrogen atom and the other is methyl, and guanidinocarbonyl group bonds at the 7-position of the benzoxazine ring]:

Guanidine hydrochloride (7.50 g) was added to a solution of sodium methoxide in methanol prepared from sodium (1.83 g) and methanol (35 ml). The mixture was stirred under reflux for 30 minutes and then filtered while heating. To the filtrate was added 7-methoxycarbonyl-2-methyl-4-(2-propyl)-3-oxo-3,4-dihydro-2H-1,4-benzoxazine (prepared in Preparation 3) (2.50 g) and the mixture was stirred under reflux for 3 hours. After concentrating the reaction mixture, water was added and extraction with ethyl acetate was conducted. The solvent was distilled off under reduced pressure and the obtained crystals were recrystallized from isopropanol to give the title compound (0.38 g) as a colorless product.

Melting point: 228°–230° C.

NMR (60 MHz, DMSO-$d_6$) δ: 1.52 (3H, d, J=6 Hz), 1.58 (6H, d, J=6 Hz), 4.65 (1H, q, J=6 Hz), 4.65–5.10 (1H, m), 7.20 (1H, d, J=8 Hz), 7.00–7.50 (4H, b), 7.95 (1H, d, J=1 Hz), 7.97 (1H, dd, J=8 Hz, 1 Hz).

Elementary Analysis for $C_{14}H_{18}N_4O_3$: Calculated (%): C,57.92; H,6.25; N,19.30 Found (%): C,57.94; H,6.30; N,19.25

EXAMPLE 3

Preparation of N-amidino-4-(2-propyl)-3-oxo-3,4-dihydro-2H-1,4-benzoxazine-7-carboxamide [the compound (I) wherein $R^1$ is 2-propyl, both $R^2$ and $R^3$ are hydrogen atom, and guanidinocarbonyl group bonds at the 7-position of the benzoxazine ring]:

Guanidine hydrochloride (3.15 g) was added to a solution of sodium methoxide in methanol prepared from sodium (0.77 g) and methanol (15 ml). The mixture was stirred under reflux for 30 minutes and then filtered while heating. To the filtrate was added 7-methoxycarbonyl-4-(2-propyl)-3-oxo-3,4-dihydro-2H-1,4-benzoxazine (prepared in Preparation 4) (0.30 g) and the mixture was stirred under reflux for 1 hour. The crystals were taken by filtration and then washed with methanol to give the title compound (0.20 g) as a colorless product.

Melting point: 235°–237° C.

NMR (60 MHz, DMSO-$d_6$) δ: 1.58 (6H, d, J=7 Hz), 4.42 (2H, s), 4.40–4.90 (1H, m), 7.12 (1H, d, J=7 Hz), 7.70 (1H, d, J=1 Hz), 7.80 (1H, dd, J=7 Hz, 1 Hz), 8.0 (4H, s).

Elementary Analysis for $C_{13}H_{16}N_4O_3$: Calculated (%): C,56.51; H,5.84; N,20.28 Found (%): C,56.32; H,5.84; N,20.34

EXAMPLE 4

Preparation of N-amidino-4-ethyl-2-methyl-3-oxo-3,4-dihydro-2H-1,4-benzoxazine-7-carboxamide [the compound (I) wherein $R^1$ is ethyl, either one of $R^2$ and $R^3$ is hydrogen atom and the other is methyl, and guanidinocarbonyl group bonds at the 7-position of the benzoxazine ring]:

Guanidine hydrochloride (7.50 g) was added to a solution of sodium methoxide in methanol prepared from 60% sodium hydride (in oil) (0.95 g) and methanol (20 ml). The mixture was stirred under reflux for 30 minutes and then filtered while heating. To the filtrate was added a solution of 4-ethyl-7-methoxycarbonyl-2-methyl-3-oxo-3,4-dihydro-2H-1,4-benzoxazine (prepared in Preparation 5) (0.85 g) in 1,2-dimethoxyethane (20 ml) and the mixture was stirred under reflux for 14 hours. After concentrating the reaction mixture, water was added and extraction with ethyl acetate was conducted. The solvent was distilled off under reduced pressure and the obtained residues were subjected to column chromatography using chloroform/methanol [5:1 (v/v)]. The obtained crystals were recrystallized from chloroform to give the title compound (0.65 g) as a colorless product.

Melting point: 219°–221° C.

NMR (300 MHz, DMSO-$d_6$) δ:1.16 (3H, t, J=7.4 Hz), 1.42 (3H, d, J=8.4 Hz), 3.67–4.00 (2H, m), 4.70 (1H, q, J=8.4 Hz), 6.20–8.40 (4H, b), 7.21 (1H, d, J=9.0 Hz), 7.88 (1H, d, J=1,5 Hz), 7.79 (1H, dd, J=9.0 Hz, 1.5 Hz).

Elementary Analysis for $C_{13}H_{16}N_4O_3$: Calculated (%): C,56.51; H,5.84; N,20.28 Found (%): C,56.43; H,5.81; N,20.15

EXAMPLE 5

Preparation of N-amidino-2,2-dimethyl-4-(2-propyl)-3-oxo-3,4-dihydro-2H-1,4-benzoxazine-6-carboxamide hydrochloride [hydrochloride of the compound (I) wherein $R^1$ is 2-propyl, both $R^2$ and $R^3$ are methyl, and guanidinocarbonyl group bonds at the 6-position of the benzoxazine ring]:

Guanidine hydrochloride (3.15 g) was added to a solution of sodium methoxide in methanol prepared from sodium (0.77 g) and methanol (15 ml). The mixture was stirred under reflux for 30 minutes and then filtered while heating. To the filtrate was added 2,2-dimethyl-6-methoxycarbonyl-4-(2-propyl)-3-oxo-3,4-dihydro-2H-1,4-benzoxazine (prepared in Preparation 6) (1.05 g) and the mixture was stirred under reflux for 3 hours. After concentrating the reaction mixture, water was added and extraction with ethyl acetate was conducted. The solvent was distilled off under reduced pressure and the obtained product was converted to a hydrochloride with 10% hydrogen chloride in ethanol. The obtained crystals were recrystallized from isopropanol to give the title compound (0.14 g) as a colorless product.

Melting point: 262°–264° C.

NMR (60 MHz, DMSO-$d_6$) δ: 1.47 (6H, s), 1.60 (6H, d, J=6 Hz), 4.70–5.10 (1H, m), 7.12 (1H, d, J=7 Hz), 7.90 (1H, dd, J=7 Hz, 1 Hz), 8.10 (1H, d, J=1 Hz), 8.34–9.30 (5H, b).

Elementary Analysis for $C_{15}H_{20}N_4O_3 \cdot HCl$: Calculated (%): C,52.86; H,6.21; N,16.44 Found (%): C,52.88; H,6.13; N,16.39

EXAMPLE 6

Preparation of N-amidino-4-ethyl-2-methyl-3-oxo-3,4-dihydro-2H-1,4-benzoxazine-6-carboxamide [the compound (I) wherein $R^1$ is ethyl, either one of $R^2$ and $R^3$ is hydrogen atom and the other is methyl, and guanidinocarbonyl group bonds at the 6-position of the benzoxazine ring]:

Guanidine hydrochloride (5.00 g) was added to a solution of sodium methoxide in methanol prepared from sodium (1.22 g) and methanol (20 ml). The mixture was stirred under reflux for 30 minutes and then filtered while heating. To the filtrate was added a solution of 4-ethyl-6-methoxycarbonyl-2-methyl-3-oxo-3,4-dihydro-2H-1,4-benzoxazine (prepared in Preparation 7) (1.80 g) in 1,2-dimethoxyethane (15 ml) and the mixture was stirred under reflux for 2 hours. The solvent was distilled off under reduced pressure and the obtained residues were subjected to column chromatography using chloroform/methanol [3:1 (v/v)]. The obtained crystals were recrystallized from acetonitrile to give the title compound (1.20 g) as a colorless product.

Melting point: 208–211° C.

NMR (60 MHz, DMSO-$d_6$) δ: 1.20 (3H, t, J=7 Hz), 1.83 (3H, d, J=8 Hz), 3.85 (2H, q, J=7 Hz), 4.58 (1H, q, J=8 Hz), 6.85 (1H, d, J=8 Hz), 7.20–7.50 (4H, b), 7.69 (1H, dd, J=8 Hz, 1 Hz), 7.76 (1H, d, J=1 Hz).

Elementary Analysis for $C_{13}H_{16}N_4O_3$: Calculated (%): C,56.51; H,5.84; N,20.28 Found (%): C,56.42; H,5.87; N,20.42

EXAMPLE 7

Preparation of N-amidino-2,2-dimethyl-4-ethyl-3-oxo-3,4-dihydro-2H-1,4-benzoxazine-6-carboxamide [the compound (I) wherein $R^1$ is ethyl, both $R^2$ and $R^3$ are methyl, and guanidinocarbonyl group bonds at the 6-position of the benzoxazine ring]:

Guanidine hydrochloride (4.40 g) was added to a solution of sodium methoxide in methanol prepared from sodium (0.90 g) and methanol (20 ml). The mixture was stirred under reflux for 30 minutes and then filtered while heating. To the filtrate was added a solution of 2,2-dimethyl-4-ethyl-6-methoxycarbonyl-3-oxo-3,4-dihydro-2H-1,4-benzoxazine (prepared in Preparation 8) (1.50 g) in 1,2-dimethoxyethane (30 ml) and the mixture was stirred under reflux for 4 hours. The solvent was distilled off under reduced pressure and the obtained residues were subjected to column chromatography using chloroform/methanol [10:1 (v/v)]. The obtained crystals were recrystallized from ethyl acetate to give the title compound (0.85 g) as a colorless product.

Melting point: 182°–185° C.

NMR (60 MHz, DMSO-$d_6$) δ: 1.21 (3H, t, J=6 Hz), 1.50 (6H, s), 4.10 (2H, q, J=6 Hz), 7.05 (1H, d, J=7 Hz), 7.90 (1H, dd, J=7 Hz, 2 Hz), 7.97 (1H, d, J=2 Hz), 7.60–8.80 (4H, b).

Elementary Analysis for $C_{14}H_{18}N_4O_3$: Calculated (%): C,57.92; H,6.25; N,19.30 Found (%): C,57.93; H,6.26; N,19.30

EXAMPLE 8

Preparation of N-amidino-2-methyl-3-oxo-3,4-dihydro-2H-1,4-benzoxazine-7-carboxamide [the compound (I) wherein $R^1$ is hydrogen, either one of $R^2$ and $R^3$ is hydrogen atom and the other is methyl, and guanidinocarbonyl group bonds at the 7-position of the benzoxazine ring]:

Guanidine hydrochloride (5.20 g) was added to a solution of sodium methoxide in methanol prepared from 60% sodium hydride (in oil) (1.90 g) and methanol (40 ml). The mixture was stirred under reflux for 30 minutes and then filtered while heating. To the filtrate was added a solution of 7-methoxycarbonyl-2-methyl-3-oxo-3,4-dihydro-2H-1,4-benzoxazine (prepared in Preparation 1) (1.50 g) in 1,2-dimethoxyethane (50 ml) and the mixture was stirred under reflux for 12 hours. The solvent was distilled off under reduced pressure and the obtained residues were subjected to column chromatography using chloroform/methanol [10:1 (v/v)]. The obtained crystals were recrystallized from methanol to give the title compound (0.25 g) as a colorless product.

Melting point: 253°–255° C.

NMR (300 MHz, DMSO-$d_6$) δ:1.41 (3H, d, J=6.6 Hz), 4.66 (1H, q, J=6.6 Hz), 6.50–8.00 (4H, b), 6.73 (1H, d, J=8.1 Hz), 7.62 (1H, s), 7.67 (1H, d, J=8.1 Hz), 10.80 (1H, s).

EXAMPLE 9

Preparation of N-amidino-2-ethyl-4-(2-propyl)-3-oxo-3,4-dihydro-2H-1,4-benzoxazine-7-carboxamide [the compound (I) wherein $R^1$ is 2-propyl, either one of $R^2$ and $R^3$ is hydrogen atom and the other is ethyl, and guanidinocarbonyl group bonds at the 7-position of the benzoxazine ring]:

Guanidine hydrochloride (12.0 g) was added to a solution of sodium methoxide in methanol prepared from sodium (2.70 g) and methanol (52 ml). The mixture was stirred under reflux for 30 minutes and then filtered while heating. To the filtrate was added 2-ethyl-7-methoxycarbonyl-4-(2-propyl)-3-oxo-3,4-dihydro-2H-1,4-benzoxazine (prepared in Preparation 9) (4.00 g) and the mixture was stirred under reflux for 3 hours. After concentrating the reaction mixture, water was added and extraction with ethyl acetate was conducted. The solvent was distilled off under reduced pressure and the obtained crystals were recrystallized from acetonitrile to give the title compound (1.25 g) as a colorless product.

Melting point: 192°–195° C.

NMR (60 MHz, DMSO-$d_6$) δ: 1.09 (3H, t, J=6 Hz), 1.59 (6H, d, J=6 Hz), 1.60–2.10 (2H, m), 4.30 (1H, t, J=6 Hz), 4.50–5.10 (1H, m), 7.19 (1H, d, J=7 Hz), 7.90 (1H, s), 7.95 (1H, d, J=7 Hz).

NMR (300 MHz, CDCl$_3$) δ: 1.05 (3H, t, J=7.9 Hz), 1.53 (3H, d, J=7.0 Hz), 1.54 (3H, d, J=7.0 Hz), 1.60–2.00 (2H, m), 4.34 (1H, dd, J=8.8 Hz, 4.4 Hz), 4.70–4.90 (1H, m), 6.00–7.00 (4H, b), 7.11 (1H, d, J=7.7 Hz), 7.82 (1H, d, J=1.3 Hz), 7.85 (1H, dd, J=7.7 Hz, 1.3 Hz).

Elementary Analysis for C$_{15}$H$_{20}$N$_4$O$_3$: Calculated (%): C,59.20; H,6.62; N,18.41 Found (%): C,58.96; H,6.60; N,18.61

EXAMPLE 10

Preparation of N-amidino-4-cyclopentyl-2-methyl-3-oxo-3,4-dihydro-2H-1,4-benzoxazine-7-carboxamide [the compound (I) wherein R$^1$ is cyclopentyl, either one of R$^2$ and R$^3$ is hydrogen atom and the other is methyl, and guanidinocarbonyl group bonds at the 7-position of the benzoxazine ring]:

Guanidine hydrochloride (7.54 g) was added to a solution of sodium methoxide in methanol prepared from sodium (1.83 g) and methanol (35 ml). The mixture was stirred under reflux for 30 minutes and then filtered while heating. To the filtrate was added 4-cyclopentyl-7-methoxycarbonyl-2-methyl-3-oxo-3,4-dihydro-2H-1,4-benzoxazine (prepared in Preparation 10) (2.20 g) and the mixture was stirred under reflux for 3 hours. After concentrating the reaction mixture, water was added and extraction with ethyl acetate was conducted. The solvent was distilled off under reduced pressure and the obtained residues were subjected to column chromatography using chloroform/methanol [10:1 (v/v)]. The obtained crystals were recrystallized from acetonitrile to give the title compound (0.35 g) as a colorless product.

Melting point: 208°–209° C.

NMR (300 MHz, DMSO-d$_6$) δ: 1.39 (3H, d, J=7.8 Hz), 1.49–1.69 (2H, m), 1.80–2.20 (6H, m), 4.57 (1H, q, J=7.8 Hz), 4.60–4.80 (1H, m), 7.26 (1H, d, J=8.7 Hz), 7.71 (1H, d, J=2.4 Hz), 7.76 (1H, dd, J=8.7 Hz, 2.4 Hz), 6.40–7.00 (2H, b), 7.50–8.20 (2H, b).

Elementary Analysis for C$_{16}$H$_{20}$N$_4$O$_3$: Calculated (%): C,60.75; H,6.37; N,17.71 Found (%): C,60.83; H,6.35; N,17.76

EXAMPLE 11

Preparation of N-amidino-2-butyl-4-(2-propyl)-3-oxo-3,4-dihydro-2H-1,4-benzoxazine-7-carboxamide hydrochloride [hydrochloride of the compound (I) wherein R$^1$ is 2-propyl, either one of R$^2$ and R$^3$ is hydrogen atom and the other is butyl, and guanidinocarbonyl group bonds at the 7-position of the benzoxazine ring]:

Guanidine hydrochloride (7.54 g) was added to a solution of sodium methoxide in methanol prepared from sodium (1.83 g) and methanol (35 ml). The mixture was stirred under reflux for 30 minutes and then filtered while heating. To the filtrate was added 2-butyl-7-methoxycarbonyl-4-(2-propyl)-3-oxo-3,4-dihydro-2H-1,4-benzoxazine (prepared in Preparation 11) (2.20 g) and the mixture was stirred under reflux for 4 hours. After concentrating the reaction mixture, water was added and extraction with ethyl acetate was conducted. The solvent was distilled off under reduced pressure and the obtained residues were subjected to column chromatography using chloroform/methanol [10:1 (v/v)]. The obtained product was converted to a hydrochloride with 10% hydrogen chloride in ethanol. The obtained crystals were washed with ethyl acetate to give the title compound (0.65 g).

NMR (60 MHz, CDCl$_3$) δ: 0.70–1.10 (3H, m), 1.51 (6H, d, J=7 Hz), 1.11–2.10 (6H, m), 4.20–5.00 (2H, m), 7.10 (1H, d, J=9 Hz), 7.76 (1H, d, J=1 Hz), 7.86 (1H, dd, J=9 Hz, 1 Hz), 6.55–7.40 (4H, b).

Elementary Analysis for C$_{17}$H$_{24}$N$_4$O$_3$.HCl-1/2H$_2$O: Calculated (%): C,54.03; H,6.93; N,14.83 Found (%): C,54.20; H,6.74; N,15.04

EXAMPLE 12

Preparation of N-amidino-4-ethyl-3-oxo-3,4-dihydro-2H-1,4-benzoxazine-7-carboxamide [the compound (I) wherein R$^1$ is ethyl, both R$^2$ and R$^3$ are hydrogen atom, and guanidinocarbonyl group bonds at the 7-position of the benzoxazine ring]:

Guanidine hydrochloride (20.0 g) was added to a solution of sodium methoxide in methanol prepared from sodium (5.0 g) and methanol (50 ml). The mixture was stirred under reflux for 30 minutes and then filtered while heating. To the filtrate (3.0 ml) was added 4-ethyl-7-methoxycarbonyl-3-oxo-3,4-di-hydro-2H-1,4-benzoxazine (prepared in Preparation 12) (0.30 g) and the mixture was stirred under reflux for 20 minutes. The crystals were taken by filtration and then washed with methanol to give the title compound (0.22 g) as a colorless product.

Melting point: 242°–245° C.

NMR (60 MHz, DMSO-d$_6$) δ: 1.20 (3H, t, J=7 Hz), 4.00 (2H, q, J=7 Hz), 4.59 (2H, s), 7.05 (1H, d, J=9 Hz), 7.69 (1H, d, J=1 Hz), 7, 80 (1H, dd, J=9 Hz, 1 Hz), 8.10 (4H, s).

Elementary Analysis for C$_{12}$H$_{14}$N$_4$O$_3$: Calculated (%): C,54.96; H,5.38; N,21.36 Found (%): C,54.77; H,5.41; N,21.56

EXAMPLE 13

Preparation of N-amidino-2,4-diethyl-3-oxo-3,4-dihydro-2H-1,4-benzoxazine-7-carboxamide [the compound (I) wherein R$^1$ is ethyl, either one of R$^2$ and R$^3$ is hydrogen atom and the other is ethyl, and guanidinocarbonyl group bonds at the 7-position of the benzoxazine ring]:

Guanidine hydrochloride (15.0 g) was added to a solution of sodium methoxide in methanol prepared from sodium (2.70 g) and methanol (55 ml). The mixture was stirred under reflux for 30 minutes and then filtered while heating. The solvent was distilled off under reduced pressure and to the residue (5.7 g) was added a solution of 2,4-diethyl-7-methoxycarbonyl-3-oxo-3,4-dihydro-2H-1,4-benzoxazine (prepared in Preparation 13) (3.00 g) in 1,2-dimethoxyethane (10 ml) and the mixture was stirred under reflux for 3 hours. After concentrating the reaction mixture, water was added and extraction with ethyl acetate was conducted. The solvent was distilled off under reduced pressure and the obtained crystals were recrystallized from acetonitrile to give the title compound (1.70 g).

Melting point: 190°–192° C.

NMR (250 MHz, DMSO-d$_6$) δ:0.98 (3H, t, J=7 Hz), 1.15 (3H, t, J=7 Hz), 1.55–1.95 (2H, m), 3.80–4.05 (2H, m), 4.40–4.60 (1H, m), 7.18 (1H, d, J=8 Hz), 7.68 (1H, d, J=2 Hz), 7.77 (1H, dd, J=8 Hz, 2 Hz), 6.20–8.40 (4H, b).

Elementary Analysis for C$_{14}$H$_{18}$N$_4$O$_3$: Calculated (%): C,57.92; H,6.25; N,19.30 Found (%): C,58.09; H,6.12; N,19.31

EXAMPLE 14

Preparation of (S)-N-amidino-2-ethyl-4-(2-propyl)-3-oxo-3,4-dihydro-2H-1,4-benzoxazine-7-carboxamide [(S)-form of the compound (I) prepared in Example 9 wherein R$^1$ is 2-propyl, either one of R² and R³ is hydrogen atom and the other is ethyl, and guanidinocarbonyl group bonds at the 7-position of the benzoxazine ring]:

Guanidine hydrochloride (15.0 g) was added to a solution of sodium methoxide in methanol prepared from sodium (2.70 g) and methanol (55 ml). The mixture was stirred under reflux for 30 minutes and then filtered while heating. The solvent was distilled off under reduced pressure and to the residue (1.09 g) was added a solution of (S)-2-ethyl-4-(2-propyl)-3-oxo-3,4-dihydro-2H-1,4-benzoxazine-7-carbonyl chloride (prepared in Preparation 14) (0.70 g) in 1,2-dimethoxyethane (5 ml) under ice cooling and the mixture was stirred for 10 minutes. After concentrating the reaction mixture, water was added and extraction with ethyl acetate was conducted. The solvent was distilled off under reduced pressure and the obtained crystals were recrystallized from acetonitrile to give the title compound (0.12 g).

Melting point: 198°–199° C.

$[\alpha]_D=+17°$ (c=1, MeOH)

NMR (300 MHz, DMSO-$d_6$) δ: 1.05 (3H, t, J=7.4 Hz), 1.52 (3H, d, J=7.0 Hz), 1.53 (3H, d, J=7.0 Hz), 1.70–2.10 (2H, m), 4.34 (1H, dd, J=8.2 Hz, 4.2 Hz), 4.70–5.90 (1H, m), 6.10–6.90 (4H, b), 7.11–7.14 (1H, m), 7.82–7.85 (2H, m).

Elementary Analysis for $C_{15}H_{20}N_4O_3$: Calculated (%): C,59.20; H,6.62; N,18.41 Found (%): C,58.92; H,6.57; N,18.49

EXAMPLE 15

Preparation of (R)-N-amidino-2-ethyl-4-(2-propyl)-3-oxo-3,4-dihydro-2H-1,4-benzoxazine-7-carboxamide [(R)-form of the compound (I) prepared in Example 9 wherein R¹ is 2-propyl, either one of R² and R³ is hydrogen atom and the other is ethyl, and guanidinocarbonyl group bonds at the 7-position of the benzoxazine ring]:

Guanidine hydrochloride (15.0 g) was added to a solution of sodium methoxide in methanol prepared from sodium (2.70 g) and methanol (55 ml). The mixture was stirred under reflux for 30 minutes and then filtered while heating. The solvent was distilled off under reduced pressure and to the residue (2.47 g) was added a solution of (R)-2-ethyl-4-(2-propyl)-3-oxo-3,4-dihydro-2H-1,4-benzoxazine-7-carbonyl chloride (prepared in Preparation 15) (1.70 g) in 1,2-dimethoxyethane (10 ml) under ice cooling and the mixture was stirred for 10 minutes. After concentrating the reaction mixture, water was added and extraction with ethyl acetate was conducted. The solvent was distilled off under reduced pressure and the obtained crystals were recrystallized from acetonitrile to give the title compound (0.60 g).

Melting point: 199°–200° C.

$[\alpha]_D=-19°$ (c=1, MeOH)

Optical purity: 94% ee

NMR (300 MHz, DMSO-$d_6$) δ:1.06 (3H, t, J=7.4 Hz), 1.52 (3H, d, J=7.0 Hz), 1.54 (3H, d, J=7.0 Hz), 1.70–2.00 (2H, m), 4.34 (1H, dd, J=8.8 Hz, 4.2 Hz), 4.70–4.85 (1H, m), 6.00–6.50 (4H, b), 7.10–7.13 (1H, m), 7.82–7.85 (2H, m).

Elementary Analysis for $C_{15}H_{20}N_4O_3$: Calculated (%): C,59.20; H,6.62; N,18.41 Found (%): C,59.20; H,6.59; N,18.59

EXAMPLE 16

Preparation of (S)-N-amidino-2,4-diethyl-3-oxo-3,4-dihydro-2H-1,4-benzoxazine-7-carboxamide [(S)-form of the compound (I) prepared in Example 13 wherein R¹ is ethyl, either one of R² and R³ is hydrogen atom and the other is ethyl, and guanidinocarbonyl group bonds at the 7-position of the benzoxazine ring]:

Guanidine hydrochloride (3.37 g) was added to a solution of sodium methoxide in methanol prepared from sodium (0.71 g) and methanol (20 ml). The mixture was stirred under reflux for 30 minutes and then filtered while heating. The solvent was distilled off under reduced pressure and to the residue was added a solution of (S)-2,4-diethyl-3-oxo-3,4-dihydro-2H-1,4-benzoxazine-7-carbonyl chloride (prepared in Preparation 16) (1.14 g) in 1,2-dimethoxyethane (20 ml) under ice cooling and the mixture was stirred for 30 minutes. After concentrating the reaction mixture, water was added and extraction with ethyl acetate was conducted. The solvent was distilled off under reduced pressure and the obtained crystals were recrystallized from acetonitrile to give the title compound (0.57 g).

Melting point: 181°–182° C.

$[\alpha]_D=+18°$ (c=1, MeOH)

Optical purity: 98% ee

NMR (250 MHz, CDCl$_3$) δ: 1.07 (3H, t, J=8 Hz), 1.27 (3H, t, J=7 Hz), 1.75–1.94 (2H, m), 3.99 (2H, q, J=7 Hz), 4.47 (1H, dd, J=9 Hz, 5 Hz), 6.10–6.80 (4H, b), 6.98 (1H, d, J=9 Hz), 7.82 (1H, d, J=2 Hz), 7.86 (1H, dd, J=9 Hz, 2 Hz).

Elementary Analysis for $C_{14}H_{18}N_4O_3$: Calculated (%): C,57.92; H,6.25; N,19.30 Found (%): C,57.95; H,6.22; N,19.33

EXAMPLE 17

Preparation of(R)-N-amidino-2,4-diethyl-3-oxo-3,4-dihydro-2H-1,4-benzoxazine-7-carboxamide [(R)-form of the compound (I) prepared in Example 13 wherein R¹ is ethyl, either one of R² and R³ is hydrogen atom and the other is ethyl, and guanidinocarbonyl group bonds at the 7-position of the benzoxazine ring]:

Guanidine hydrochloride (3.10 g) was added to a solution of sodium methoxide in methanol prepared from sodium (0.65 g) and methanol (20 ml). The mixture was stirred under reflux for 30 minutes and then filtered while heating. The solvent was distilled off under reduced pressure and to the residue was added a solution of (R)-2,4-diethyl-3-oxo-3,4-dihydro-2H-1,4-benzoxazine-7-carbonyl chloride (prepared in Preparation 17) (1.14 g) in 1,2-dimethoxyethane (5 ml) under ice cooling and the mixture was stirred for 10 minutes. After concentrating the reaction mixture, water was added and extraction with ethyl acetate was conducted. The solvent was distilled off under reduced pressure and the obtained crystals were recrystallized from acetonitrile to give the title compound (0.70 g).

Melting point: 181°–182° C.

$[\alpha]_D=-19°$ (c=1, MeOH)

NMR (250 MHz, CDCl$_3$) δ: 1.07 (3H, t, J=8 Hz), 1.27 (3H, t, J=8 Hz), 1.70–2.00 (2H, m), 3.99 (2H, q, J=8 Hz), 4.47 (1H, dd, J=9 Hz, 5 Hz), 6.00–6.90 (4H, b), 6.98 (1H, d, J=9 Hz), 7.82 (1H, d, J=2 Hz), 7.86 (1H, dd, J=9Hz, 2Hz).

Elementary Analysis for $C_{14}H_{18}N_4O_3$: Calculated (%): C,57.92; H,6.25; N,19.30 Found (%): C,57.78; H,6.21; N,19.34

EXAMPLE 18

Preparation of (R)-N-amidino-2-ethyl-4-(2-propyl)-3-oxo-3,4-dihydro-2H-1,4-benzoxazine-7-carboxamide hydrochloride [hydrochloride of the compound (I) prepared in Example 15 wherein $R^1$ is 2-propyl, either one of $R^2$ and $R^3$ is hydrogen atom and the other is ethyl, and guanidinocarbonyl group bonds at the 7-position of the benzoxazine ring]:

To a solution of (R)-N-amidino-2-ethyl-4-(2-propyl)-3-oxo-3,4-dihydro-2H-1,4-benzoxazine-7-carboxamide prepared in Example 15 (0.45 g) in methanol (10 ml) was added a 14% solution of hydrogen chloride in ethyl acetate (0.37 ml). Then, the solvent was distilled off under reduced pressure and the obtained crystals were recrystallized from ethanol to give the title compound (0.27 g) as a colorless product.

Melting point: 220°–221° C.

$[\alpha]_D = -18°$ (c=1, MeOH)

NMR (250 MHz, CDCl$_3$) δ: 1.05 (3H, t, J=7 Hz), 1.53 (3H, d, J=7 Hz), 1.57 (3H, d, J=7 Hz), 1.76–1.89 (2H, m), 4.40 (1H, dd, J=9 Hz, 5 Hz), 4.69–4.77 (1H, m), 7.22 (1H, d, J=8 Hz), 7.88 (1H, d, J=2 Hz), 8.00 (1H, dd, J=9 Hz, 2 Hz), 8.57 (2H, s), 8.97 (2H, s), 11.45 (1H, s).

Elementary Analysis for $C_{15}H_{20}N_4O_3 \cdot HCl$: Calculated (%): C,52.86; H,6.21; N,16.44 Found (%): C,52.79; H,6.19; N,16.49

EXAMPLE 19

Preparation of (R)-N-amidino-2-ethyl-4-(2-propyl)-3-oxo-3,4-dihydro-2H-1,4-benzoxazine-7-carboxamide methanesulfonate [methanesulfonate of the compound (I) prepared in Example 15 wherein $R^1$ is 2-propyl, either one of $R^2$ and $R^3$ is hydrogen atom and the other is ethyl, and guanidinocarbonyl group bonds at the 7-position of the benzoxazine ring]:

To a suspension of (R)-N-amidino-2-ethyl-4-(2-propyl)-3-oxo-3,4-dihydro-2H-1,4-benzoxazine-7-carboxamide prepared in Example 15 (0.089 g) in methanol (6 ml) was added a 0.05M solution of methanesulfonic acid in methanol (5.8 ml). Then, after the mixture was heated to dissolve, the solvent was distilled off under reduced pressure and the obtained crystals were recrystallized from acetonitrile to give the title compound (0.10 g) as a colorless product.

Melting point: 170°–171° C.

$[\alpha]_D = -16°$ (c=1, MeOH)

NMR (250 MHz, DMSO-d$_6$) δ: 1.00 (3H, t, J=7 Hz), 1.47 (6H, d, J=7 Hz), 1.69–1.86 (2H, m), 2.44 (3H, s), 4.54 (1H, dd, J=8 Hz, 5 Hz), 4.70–4.80 (1H, m), 7.53 (1H, d, J=9 Hz), 7.63 (1H, d, J=2 Hz), 7.71 (1H, dd, J=9 Hz, 2 Hz), 8.20–8.60 (4H, b), 11.19 (1H, s).

Elementary Analysis for $C_{15}H_{20}N_4O_3 \cdot CH_3SO_3H$: Calculated (%): C,47.99; H,6.04; N,13.99 Found (%): C,48.05; H,6.05; N,13.85

EXAMPLE 20

Preparation of (S)-N-amidino-2,4-diethyl-3-oxo-3,4-dihydro-2H-1,4-benzoxazine-7-carboxamide hydrochloride [hydrochloride of the compound (I) prepared in Example 16 wherein $R^1$ is ethyl, either one of $R^2$ and $R^3$ is hydrogen atom and the other is ethyl, and guanidinocarbonyl group bonds at the 7-position of the benzoxazine ring]:

To a solution of (S)-N-amidino-2,4-diethyl-3-oxo-3,4-dihydro-2H-1,4-benzoxazine-7-carboxamide prepared in Example 16 (0.37 g) in methanol (6 ml) was added a 14% solution of hydrogen chloride in ethyl acetate (0.32 ml). Then, the solvent was distilled off under reduced pressure and the obtained crystals were recrystallized from isopropanol to give the title compound (0.14 g) as a colorless product.

Melting point: 197°–199° C.

$[\alpha]_D = +20°$ (c=1, MeOH)

NMR (250 MHz, CDCl$_3$) δ: 1.06 (3H, t, J=7 Hz), 1.26 (3H, t, J=7 Hz), 1.70–2.00 (2H, m), 3.99 (2H, q, J=7 Hz), 4.52 (1H, dd, J=8 Hz, 5 Hz), 7.08 (1H, d, J=9 Hz), 7.88 (1H, d, J=2 Hz), 8.02 (1H, dd, J=9 Hz, 2 Hz), 8.58 (2H, s), 8.98 (2H, s), 11.48 (1H, s).

Elementary Analysis for $C_{14}H_{18}N_4O_3 \cdot HCl$: Calculated (%): C,51.46; H,5.86; N,17.14 Found (%): C,51.46; H,5.90; N,17.05

EXAMPLE 21

Preparation of (S)-N-amidino-2,4-diethyl-3-oxo-3,4-dihydro-2H-1,4-benzoxazine-7-carboxamide methanesulfonate [methanesulfonate of the compound (I) prepared in Example 16 wherein $R^1$ is ethyl, either one of $R^2$ and $R^3$ is hydrogen atom and the other is ethyl, and guanidinocarbonyl group bonds at the 7-position of the benzoxazine ring]:

To a suspension of (S)-N-amidino-2,4-diethyl-3-oxo-3,4-dihydro-2H-1,4-benzoxazine-7-carboxamide prepared in Example 16 (0.089 g) in methanol (6 ml) was added a 0.05M solution of methanesulfonic acid in methanol (6.2 ml). Then, after the mixture was heated to dissolve, the solvent was distilled off under reduced pressure and the obtained crystals were recrystallized from ethanol to give the title compound (0.096 g) as a colorless product.

Melting point: 225°–226° C.

$[\alpha]_D = +15°$ (c=1, MeOH)

NMR (250 MHz, DMSO-d$_6$) δ: 1.01 (3H, t, J=7 Hz), 1.17 (3H, t, J=7 Hz), 1.74–1.90 (2H, m), 2.43 (3H, s), 3.99 (2H, q, J=7 Hz), 4.67 (1H, dd, J=8 Hz, 5 Hz), 7.42 (1H, d, J=9 Hz), 7.61 (1H, d, J=2 Hz), 7.72 (1H, dd, J=9 Hz, 2 Hz), 8.20–8.60 (4H, b), 11.61 (1H, s).

Elementary Analysis for $C_{14}H_{18}N_4O_3 \cdot CH_3SO_3H$: Calculated (%): C,46.62; H,5.74; N,14.50 Found (%): C,46.66; H,5.76; N,14.35

EXAMPLE 22

Preparation of N-amidino-2,2-dimethyl-4-(2-propyl)-3-oxo-3,4-dihydro-2H-1,4-benzoxazine-6-carboxamide [the compound (I) wherein $R^1$ is 2-propyl, both $R^2$ and $R^3$ are methyl, and guanidinocarbonyl group bonds at the 6-position of the benzoxazine ring]:

To a suspension of N-amidino-2,2-dimethyl-4-(2-propyl)-3-oxo-3,4-dihydro-2H-1,4-benzoxazine-6-carboxamide hydrochloride prepared in Example 5 (3.4 g) in ethyl acetate (50 ml) and methanol (10 ml) was added a saturated aqueous sodium hydrogen carbonate solution (30 ml) and the mixture was stirred at room temperature for 30 minutes. The organic layer was separated, washed with water, dried over magnesium sulfate, and the solvent was distilled off under reduced pressure. The obtained residues were recrystallized from methanol to give the title compound (1.8 g).

Melting point: 212°–214° C.

NMR (250 MHz, CDCl$_3$) δ: 1.45 (6H, s), 1.56 (6H, d, J=7 Hz), 4.70–4.82 (1H, m), 6.10–6.70 (4H, b), 6.96 (1H, d, J=8 Hz), 7.87 (1H, dd, J=8 Hz, 2 Hz), 8.00 (1H, d, J=2 Hz).

Elementary Analysis for $C_{15}H_{20}N_4O_3$: Calculated (%): C,59.20; H,6.62; N,18.41 Found (%): C,59.02; H,6.67; N,18.45

EXAMPLE 23

Preparation of N-amidino-2,2-dimethyl-4-(2-propyl)-3-oxo-3,4-dihydro-2H-1,4-benzoxazine-6-carboxamide methanesulfonate [methanesulfonate of the compound (I) wherein $R^1$ is 2-propyl, both $R^2$ and $R^3$ are methyl, and guanidinocarbonyl group bonds at the 6-position of the benzoxazine ring (the compound of Example 22)]:

N-Amidino-2,2-dimethyl-4- (2-propyl) -3-oxo-3,4-dihydro-2H-1,4-benzoxazine-6-carboxamide as used in Example 22 (18.7 g) was dissolved in hot isopropanol (200 ml), and thereto was added methanesulfonic acid (6.0 g). After cooling, the precipitated crystals were recrystallized from isopropanol to give the title compound (13.7 g).

Melting point: 192°–194° C.

NMR (250 MHz, DMSO-$d_6$) δ: 1.41 (6H, s), 1.50 (6H, d, J=7 Hz), 2.39 (3H, s), 4.60–4.80 (1H, m), 7.20 (1H, d, J=8 Hz), 7.65 (1H, dd, J=8 Hz, 2 Hz), 7.75 (1H, d, J=2 Hz), 8.25–8.50 (4H, b), 11.22 (1H, s).

Elementary Analysis for $C_{15}H_{20}N_4O_3 \cdot CH_3SO_3H$: Calculated (%): C,47.99; H,6.04; N,14.00 Found (%): C,47.82; H,6.06; N,13.92

The compounds obtained in Examples 1 to 23 are summarized in the following Table 1.

TABLE 1

| Ex. | *1 | $R^1$ | $R^2$ | $R^3$ | |
|---|---|---|---|---|---|
| 1 | 7-position | 2-Propyl | Methyl | Methyl | |
| 2 | 7-position | 2-Propyl | Methyl | H | |
| 3 | 7-position | 2-Propyl | H | H | |
| 4 | 7-position | Ethyl | Methyl | H | |
| 5 | 6-position | 2-Propyl | Methyl | Methyl | *2 |
| 6 | 6-position | Ethyl | Methyl | H | |
| 7 | 6-position | Ethyl | Methyl | Methyl | |
| 8 | 7-position | H | Methyl | H | |
| 9 | 7-position | 2-Propyl | Ethyl | H | |
| 10 | 7-position | Cyclopentyl | H | Methyl | |
| 11 | 7-position | 2-Propyl | H | Butyl | *3 |
| 12 | 7-position | Ethyl | H | H | |
| 13 | 7-position | Ethyl | H | Ethyl | |
| 14 | 7-position | 2-Propyl | H | Ethyl | *4 |
| 15 | 7-position | 2-Propyl | H | Ethyl | *5 |
| 16 | 7-position | Ethyl | H | Ethyl | *6 |
| 17 | 7-position | Ethyl | H | Ethyl | *7 |
| 18 | 7-position | 2-Propyl | H | Ethyl | *8 |
| 19 | 7-position | 2-Propyl | H | Ethyl | *9 |
| 20 | 7-position | Ethyl | H | Ethyl | *10 |
| 21 | 7-position | Ethyl | H | Ethyl | *11 |
| 22 | 6-position | 2-Propyl | Methyl | Methyl | |
| 23 | 6-position | 2-Propyl | Methyl | Methyl | *12 |

(Note)
*1: The position where the guanidinocarbonyl group is attached to the benzoxazine ring
*2: Hydrochloride
*3: Hydrochloride
*4: (S)-Form of the compound of Example 9
*5: (R)-Form of the compound of Example 9
*6: (S)-Form of the compound of Example 13
*7: (R)-Form of the compound of Example 13
*8: Hydrochloride of the compound of Example 15
*9: Methanesulfonate of the compound of Example 15
*10: Hydrochloride of the compound of Example 16
*11: Methanesulfonate of the compound of Example 16
*12: Methanesulfonate of the compound of Example 22

EXAMPLE 24

Preparation of injections:

(R)-N-Amidino-2-ethyl-4-(2-propyl)-3-oxo-3,4-dihydro-2H-1,4-benzoxazine-7-carboxamide hydrochloride (1 g) prepared in Example 18 was dissolved in purified water for injections to give a total amount of 1000 ml. This solution was sterilized by filtration with a membrane filter (0.2 µm) and each 1 ml of the solution was poured into an ampule. The ampules were sealed and then sterilized by heating at 120° C. for 20 minutes.

EXAMPLE 25

Preparation of injections:

(R)-N-Amidino-2-ethyl-4-(2-propyl)-3-oxo-3,4-dihydro-2H-1,4-benzoxazine-7-carboxamide methanesulfonate (1 g) prepared in Example 19 was dissolved in purified water for injections to give a total amount of 1000 ml. This solution was sterilized by filtration with a membrane filter (0.2 µm) and each 1 ml of the solution was poured into an ampule. The ampules were sealed and then sterilized by heating at 120° C. for 20 minutes.

EXAMPLE 26

Preparation of injections:

(S)-N-Amidino-2,4-diethyl-3-oxo-3,4-dihydro-2H-1,4-benzoxazine-7-carboxamide hydrochloride (1 g) prepared in Example 20 was dissolved in purified water for injections to give a total amount of 1000 ml. This solution was sterilized by filtration with a membrane filter (0.2 µm) and each 1 ml of the solution was poured into an ampule. The ampules were sealed and then sterilized by heating at 120° C. for 20 minutes.

EXAMPLE 27

Preparation of injections:

(S)-N-Amidino-2,4-diethyl-3-oxo-3,4-dihydro-2H-1,4-benzoxazine-7-carboxamide methanesulfonate (1 g) prepared in Example 21 was dissolved in purified water for injections to give a total amount of 1000 ml. This solution was sterilized by filtration with a membrane filter (0.2 µm) and each 1 ml of the solution was poured into an ampule. The ampules were sealed and then sterilized by heating at 120° C. for 20 minutes.

EXAMPLE 28

Preparation of tablets:

| Component | Amount (g) |
|---|---|
| (R)-N-Amidino-2-ethyl-4-(2-propyl)-3-oxo-3,4-dihydro-2H-1,4-benzoxazine-7-carboxamide hydrochloride prepared in Example 18 | 5 |
| Lactose | 77.5 |
| Corn starch | 28 |
| Crystalline cellulose | 25 |
| Hydroxypropylcellulose | 3.5 |
| Magnesium stearate | 1 |
| Total | 140 |

The above components were mixed together and compressed with a tablet machine to give tablets (each weighing 140 mg).

EXAMPLE 29

Preparation of tablets:

| Component | Amount (g) |
| --- | --- |
| (R)-N-Amidino-2-ethyl-4-(2-propyl)-3-oxo-3,4-dihydro-2H-1,4-benzoxazine-7-carboxamide methanesulfonate prepared in Example 19 | 5 |
| Lactose | 77.5 |
| Corn starch | 28 |
| Crystalline cellulose | 25 |
| Hydroxypropylcellulose | 3.5 |
| Magnesium stearate | 1 |
| Total | 140 |

The above components were mixed together and compressed with a tablet machine to give tablets (each weighing 140 mg).

EXAMPLE 30

Preparation of tablets:

| Component | Amount (g) |
| --- | --- |
| (S)-N-Amidino-2,4-diethyl-3-oxo-3,4-dihydro-2H-1,4-benzoxazine-7-carboxamide hydrochloride prepared in Example 20 | 5 |
| Lactose | 77.5 |
| Corn starch | 28 |
| Crystalline cellulose | 25 |
| Hydroxypropylcellulose | 3.5 |
| Magnesium stearate | 1 |
| Total | 140 |

The above components were mixed together and compressed with a tablet machine to give tablets (each weighing 140 mg).

EXAMPLE 31

Preparation of tablets:

| Component | Amount (g) |
| --- | --- |
| (S)-N-Amidino-2,4-diethyl-3-oxo-3,4-dihydro-2H-1,4-benzoxazine-7-carboxamide methanesulfonate prepared in Example 21 | 5 |
| Lactose | 77.5 |
| Corn starch | 28 |
| Crystalline cellulose | 25 |
| Hydroxypropylcellulose | 3.5 |
| Magnesium stearate | 1 |
| Total | 140 |

The above components were mixed together and compressed with tablet machine to give tablets (each weighing 140 mg).

Experiment 1

$Na^+/H^+$ Exchange inhibitory activity:

The compounds of the present invention were assessed for their $Na^+/H^+$ exchange inhibitory activity based on an activity to inhibit sodium propionate-induced swelling of platelets in accordance with the method of Rosskoph et al. [*Journal of Hypertension*, 9, 231–238 (1991)].

(1) Test compounds:
  (i) The compounds of Examples 1 to 10 and 12 to 21
  (ii) Amiloride (control)

(2) Test procedures:

First, platelet-rich plasma was prepared in accordance with the method of Mammen et al. [Diabetes Research and Clinical Practice, 9(3), 265–272 (1990)]. Briefly, male Wistar rats weighing 190 to 420 g were abdominally operated under anesthesia with ether and blood was taken from the abdominal aorta. For inhibiting blood coagulation, ACD solution (a mixture of 65 mM citric acid, 85 mM sodium citrate, 11 mM dextrose) was added to blood and this treated blood was centrifuged at 90× g for 10 minutes. A supernatant was separated to prepare platelet-rich plasma.

Then, a solution of the test compounds in dimethylsulfoxide was added to 140 mM sodium propionate buffer solution. To this mixture was added the platelet-rich plasma prepared above and a decrease in optical density was recorded with the passage of time at 37° C. using a platelet aggregometer (turbidimeter) and a X-Y recorder to calculate a decrease rate in optical density after mixing with platelet-rich plasma [decrease rate in optical density in the presence of the test compounds (D)]. On the other hand, the solvent dimethylsulfoxide alone was used instead of the solution of the test compounds and the decrease in optical density was recorded in the similar manner to calculate a decrease rate in optical density [control (C)]. A swelling inhibitory rate (%) was calculated using the following formula:

$$\text{Swelling inhibitory rate (\%)} = (1 - D/C) \times 100$$

Then, a concentration of the test compounds which shows a 50% inhibition ($IC_{50}$) was calculated by the method of linear regression analysis.

(3) Results:

The results are shown in Table 2.

TABLE 2

| Test Compounds | $IC_{50}$ (μM) |
| --- | --- |
| Compound of Example 1 | 0.20 |
| Compound of Example 2 | 0.094 |
| Compound of Example 3 | 0.17 |
| Compound of Example 4 | 0.16 |
| Compound of Example 5 | 0.12 |
| Compound of Example 6 | 0.29 |
| Compound of Example 7 | 0.38 |
| Compound of Example 8 | 0.81 |
| Compound of Example 9 | 0.034 |
| Compound of Example 10 | 0.062 |
| Compound of Example 12 | 0.36 |
| Compound of Example 13 | 0.083 |
| Compound of Example 14 | 0.073 |
| Compound of Example 15 | 0.036 |
| Compound of Example 16 | 0.045 |
| Compound of Example 17 | 0.071 |
| Compound of Example 18 | 0.038 |
| Compound of Example 19 | 0.044 |
| Compound of Example 20 | 0.049 |
| Compound of Example 21 | 0.089 |
| Amiloride | 13 |

Experiment 2

Inhibitory activity against reperfusion arrhythmia:

Using a rat acute myocardial infarction model, the compounds of the present invention were assessed for their inhibitory activity against reperfusion arrhythmia in accordance with the method of Tagliavini et al. [European Journal of Pharmacology, 194, 7–10 (1991)].

(A) Test 1:

(1) Test compound:

(i) The compound of Example 2

(2) Test procedure:

Male Sprague-Dawley rats (weighing 310 to 490 g) were anesthetized by intraperitoneal administration of sodium pentobarbital (50 mg/kg). Under anesthesia, the rats were cannulated via trachea and the cannula was linked to a respirator. An electrocardiogram (the lead II) was obtained from electrodes attached to the limbs using bioelectric amplifier while maintaining the body temperature at 37° C. The chest of the rats were opened at the left fifth intercostal space and the pericardium was cut open to reveal the heart. Then a solution of the test compound in a mixed solvent of polyethylene glycol 400, ethanol and a physiological saline [3:3:14 (v/v)] was administered into the femoral vein. Ten minutes after the administration of the compound, the origin of the left coronary artery was occluded. After occlusion for 5 minutes, reperfusion was carried out for 10 minutes and a duration (second) of a ventricular fibrillation after reperfusion was measured from the electrocardiogram (mean±standard error, n=3 to 10). The ventricular fibrillation was assessed in accordance with the guideline of The Lambeth Convention [Cardiovascular Research, 22, 447–455 (1988)].

On the other hand, the mixed solvent of polyethylene glycol 400, ethanol and a physiological saline [3:3:14 (v/v)] alone was used as a control and a duration (second) of the ventricular fibrillation was measured in a similar manner.

(3) Results:

The results are shown in Table 3.

TABLE 3

| Test compound | Dose (mg/kg) | Duration (second) of ventricular fibrillation (mean ± standard error) |
|---|---|---|
| Control | — | 92.6 ± 20.2 |
| Compound of Example 2 | 0.01 | 118.9 ± 59.4 |
| | 0.1 | 19.1 ± 12.4* |
| | 1 | 0.0 ± 0.0* |

(Note)
*: $p < 0.05$, significantly different from the control group (Mann-Whitney U-test)

(B) Test 2:

(1) Test compounds:

(i) The compounds of Examples 5, 18 and 20

(2) Test procedure:

Using male Sprague-Dawley rats weighing 310 to 440 g, the duration (second) of the ventricular fibrillation was measured in the same manner as in Test 1 (n=4 to 10).

(3) Results:

The results are shown in Table 4.

TABLE 4

| Test compounds | Dose (mg/kg) | Duration (second) of ventricular fibrillation (mean ± standard error) |
|---|---|---|
| Control | — | 146.1 ± 5.9 |
| Compound of Example 5 | 0.1 | 80.2 ± 27.8** |
| Compound of | 0.01 | 75.5 ± 29.2 |
| Example 18 | 0.1 | 31.4 ± 20.6** |
| | 1 | 0.0 ± 0.0** |
| Compound of Example 20 | 0.1 | 27.2 ± 27.2** |

(Note)
**: $p < 0.01$, significantly different from the control group (Mann-Whitney U-test)

(C) Test 3:

(1) Test compounds:

(i) The compound of Examples 19 and 21

(2) Test procedure:

Using male Sprague-Dawley rats weighing 310 to 400 g, the duration (second) of the ventricular fibrillation was measured in the same manner as in Test 1 (n=4 to 6).

(3) Results:

The results are shown in Table 5.

TABLE 5

| Test compounds | Dose (mg/kg) | Duration (second) of ventricular fibrillation (mean ± standard error) |
|---|---|---|
| Control | — | 171.0 ± 5.8 |
| Compound of Example 19 | 0.01 | 116.8 ± 40.2 |
| | 0.1 | 36.5 ± 32.2* |
| | 1 | 0.0 ± 0.0* |
| Compound of Example 21 | 0.1 | 69.0 ± 31.1** |

(Note)
*: $p < 0.05$
**: $p < 0.01$, significantly different from the control group (Mann-Whitney U-test)

Experiment 3

Activity to reduce myocardial infarction lesion:

Using a rat acute myocardial infarction model, the compounds of the present invention were assessed for their activity to reduce myocardial infarction lesion in accordance with the method of Petty et al. [European Journal of Pharmacology, 192, 383–388 (1991)].

(A) Test 1:

(1) Test compound:

(i) The compound of Example 2

(2) Test procedure:

Male Sprague-Dawley rats (weighing 320 to 430 g) were anesthetized by intraperitoneal administration of sodium pentobarbital (50 mg/kg). Under anesthesia, the rats were cannulated via trachea and the cannula was linked to a respirator and then the body temperature was maintained at 37° C. The chest of the rats were opened at the left fifth intercostal space and the pericardium was cut open to reveal the heart. Then a solution of the test compound in a mixed solvent of polyethylene glycol 400, ethanol and a physiological saline [3:3:14 (v/v)] was administered into the femoral vein. Ten minutes after the administration of the compound, the origin of the left coronary artery was occluded. After occlusion for 30 minutes, reperfusion was carried out for 2 hours. After reperfusion, the heart was removed and the origin of the left coronary artery was ligated again. The heart was cannulated via the aorta and a 0.025% solution of Evans blue was perfused using a syringe pump to distinguish an ischemic region (not stained with Evans blue) and a non-ischemic region (stained with Evans blue). The ischemic region was incubated in a 0.1% triphenyltetrazolium chloride (TTC) solution at 37° C. for 30 minutes to distinguish a TTC-stained region and a non-stained region (infarction region). Each wet weight of these TTC-stained and non-stained regions was measured and a ratio of the infarction region (wet weight of the TTC non-stained region) to the ischemic region (wet weight of Evans blue non-stained region) was calculated and demonstrated by percent (mean±standard error, n=3 to 8).

On the other hand, the mixed solvent of polyethylene glycol 400, ethanol and a physiological saline [3:3:14 (v/v)] alone was used as a control and the ratio of the infarction region to the ischemic region was calculated in the similar manner and demonstrated by percent.

(3) Results:
The results are shown in Table 6.

TABLE 6

| Test compound | Dose (mg/kg) | Infarction region/ischemic region (%) (mean ± standard error) |
| --- | --- | --- |
| Control | — | 51.4 ± 2.4 |
| Compound of Example 2 | 0.01 | 41.7 ± 10.3 |
|  | 0.1 | 35.6 ± 3.5 |
|  | 1 | 7.2 ± 4.9** |

(Note)
**: $p < 0.01$, significantly different from the control group (Dunnett's test)

(B) Test 2:
(1) Test compound:
(i) The compound of Example 18 and 19
(2) Test procedure:
Using male Sprague-Dawley rats weighing 310 to 390 g, the ratio of the infarction region to the ischemic region was calculated in the similar manner and demonstrated by percent (n=4).
(3) Results:
The results are shown in Table 7.

TABLE 7

| Test compounds | Dose (mg/kg) | Infarction region/ischemic region (%) (mean ± standard error) |
| --- | --- | --- |
| Control | — | 45.2 ± 4.1 |
| Compound of Example 18 | 1 | 21.7 ± 5.5** |
| Compound of Example 19 | 1 | 20.7 ± 5.2** |

(Note)
**: $p < 0.01$, significantly different from the control group (Dunnett's test)

What is claimed is:
1. A 1,4-benzoxazine compound of the following formula (I):

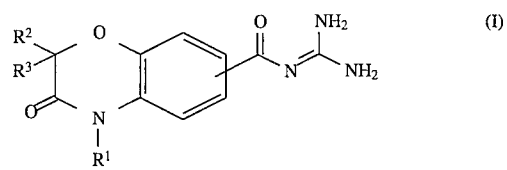

wherein $R^1$ is hydrogen atom, an alkyl group having 1 to 6 carbon atoms or a cycloalkyl group having 5 to 7 carbon atoms; $R^2$ and $R^3$ may be the same or different and are hydrogen atom or an alkyl group having 1 to 4 carbon atoms; the guanidinocarbonyl group bonds at the 6- or 7-position of the benzoxazine ring, or a pharmaceutically acceptable salt thereof.

2. The compound of claim 1 wherein $R^2$ and $R^3$ are the same or different from each other and are hydrogen atom or an alkyl group having 1 to 2 carbon atoms, or a pharmaceutically acceptable salt thereof.

3. The compound of claim 2 wherein $R^1$ is ethyl or 2-propyl, or a pharmaceutically acceptable salt thereof.

4. The compound of claim 1 which is N-amidino-2,2-dimethyl-4-(2-propyl)-3-oxo-3,4-dihydro-2H-1,4-benzoxazine-6-carboxamide, or a pharmaceutically acceptable salt thereof.

5. The compound of claim 1 which is (R)-N-amidino-2-ethyl-4-(2-propyl)-3-oxo-3,4-dihydro-2H-1,4-benzoxazine-7-carboxamide, or a pharmaceutically acceptable salt thereof.

6. The compound of claim 1 which is (S)-N-amidino-2-ethyl-4-(2-propyl)-3-oxo-3,4-dihydro-2H-1,4-benzoxazine-7-carboxamide, or a pharmaceutically acceptable salt thereof.

7. The compound of claim 1 which is (S)-N-amidino-2,4-diethyl-3-oxo-3,4-dihydro-2H-1,4-benzoxazine-7-carboxamide, or a pharmaceutically acceptable salt thereof.

8. The compound of claim 1 which is (R)-N-amidino-2,4-diethyl-3-oxo-3,4-dihydro-2H-1,4-benzoxazine-7-carboxamide, or a pharmaceutically acceptable salt thereof.

9. A pharmaceutical composition comprising the compound or a pharmaceutically acceptable salt thereof as set forth in claim 1 as an active ingredient and a pharmaceutically acceptable carrier, diluent or vehicle.

10. The pharmaceutical composition of claim 9 which is for prevention or treatment of ischemic heart disease.

11. The pharmaceutical composition of claim 10 which is for prevention or treatment of cardiac dysfunction.

12. The pharmaceutical composition of claim 10 which is for prevention or treatment of myocardial necrosis.

13. The pharmaceutical composition of claim 10 which is for prevention or treatment of arrhythmia.

14. The pharmaceutical composition of claim 9 which is a $Na^+/H^+$ exchange inhibitor.

* * * * *